United States Patent
Liu et al.

(10) Patent No.: US 11,116,726 B2
(45) Date of Patent: Sep. 14, 2021

(54) ECHINOMYCIN FORMULATION, METHOD OF MAKING AND METHOD OF USE THEREOF

(71) Applicant: CHILDREN'S RESEARCH INSTITUTE, CHILDREN'S NATIONAL MEDICAL CENTER, Washington, DC (US)

(72) Inventors: Yang Liu, Washington, DC (US); Yin Wang, Washington, DC (US); Yan Liu, Washington, DC (US); Christopher Bailey, Merritt Island, FL (US); Pan Zheng, Washington, DC (US)

(73) Assignee: CHILDRENS RESEARCH INSTITUTE, CHILDRENS NATIONAL MEDICAL CENTER, Washington, DC (US)

( * ) Notice: Subject to any disclaimer, the term of this patent is extended or adjusted under 35 U.S.C. 154(b) by 0 days.

(21) Appl. No.: 15/774,217

(22) PCT Filed: Nov. 9, 2016

(86) PCT No.: PCT/US2016/061157
§ 371 (c)(1),
(2) Date: May 7, 2018

(87) PCT Pub. No.: WO2017/083403
PCT Pub. Date: May 18, 2017

(65) Prior Publication Data
US 2018/0344642 A1 Dec. 6, 2018

Related U.S. Application Data

(60) Provisional application No. 62/253,257, filed on Nov. 10, 2015.

(51) Int. Cl.
| | |
|---|---|
| *A61K 9/127* | (2006.01) |
| *A61K 38/16* | (2006.01) |
| *A61K 47/69* | (2017.01) |
| *A61K 35/74* | (2015.01) |
| *A61P 37/02* | (2006.01) |
| *A61P 35/02* | (2006.01) |

(52) U.S. Cl.
CPC ............ *A61K 9/1271* (2013.01); *A61K 35/74* (2013.01); *A61K 38/164* (2013.01); *A61K 47/6911* (2017.08); *A61P 35/02* (2018.01); *A61P 37/02* (2018.01); *A61K 9/1277* (2013.01)

(58) Field of Classification Search
CPC ............ A61K 9/1271; A61K 47/6911; A61K 38/164; A61K 35/74; A61K 9/1277; A61K 9/19; A61K 38/08; A61P 37/02; A61P 35/02; A61P 35/00
USPC ......................................................... 424/450
See application file for complete search history.

(56) References Cited

U.S. PATENT DOCUMENTS

| 4,873,088 A * | 10/1989 | Mayhew ................ A61K 9/127 424/450 |
|---|---|---|
| 5,139,803 A * | 8/1992 | Haynes .................. A23D 7/013 426/330.6 |
| 7,419,683 B2 * | 9/2008 | Szebeni ............... A61K 38/177 424/450 |
| 9,259,392 B2 * | 2/2016 | Gould-Fogerite ........ A61P 3/06 |
| 9,849,087 B2 * | 12/2017 | Fologea .................... A61N 5/10 |
| 2004/0156888 A1 * | 8/2004 | Jensen ................... A61K 9/127 424/450 |
| 2007/0105758 A1 * | 5/2007 | May .................... A61K 31/7034 514/2.7 |
| 2007/0190633 A1 * | 8/2007 | Strobel .................. A01H 17/00 435/253.5 |
| 2008/0103213 A1 * | 5/2008 | Kurzrock ............. A61K 9/1271 514/679 |
| 2009/0053769 A1 * | 2/2009 | Wang .................... C12P 17/167 435/71.3 |
| 2009/0104257 A1 * | 4/2009 | Li .......................... A61K 9/127 424/450 |
| 2010/0008978 A1 * | 1/2010 | Drummond ............ A61K 31/00 424/450 |
| 2012/0264697 A1 | 10/2012 | Liu et al. |
| 2013/0164370 A1 * | 6/2013 | Pumeranz ............ A61K 9/1271 424/450 |

(Continued)

FOREIGN PATENT DOCUMENTS

| CN | 103157112 | 12/2014 |
|---|---|---|
| JP | 2007-511505 | 5/2007 |

(Continued)

OTHER PUBLICATIONS

Trosko J.e., et al in Mutation Research, vol. 480-481, pp. 219-229, 2001.*
Iriondo O. et al., "Distinct Breast Cancer Stem/Progenitor Cell Populations require Either HIF1alpha or Loss of PHD3 to Expand Under Hypoxic Conditions". Oncotarget, Sep. 10, 2015. vol. 6, No. 31; p. 31722, first column, fourth paragraph, second paragraph, p. 31732, first column, second paragraph.

(Continued)

*Primary Examiner* — Gollamudi S Kishore
(74) *Attorney, Agent, or Firm* — Michael Ye; Morris Manning & Martin LLP

(57) ABSTRACT

A liposomal drug formulation for treating a disease in a patient characterized by overexpression of HIF-1α and/or HIF-2α includes a plurality of liposomes in a pharmaceutically acceptable carrier. The liposomes encapsulate echinomycin and are made from a peglyated phospholipid, a neutral phosphoglyceride, and a sterol. The PEGylated liposomes may be used to treat proliferative diseases, leukemia, cancer, autoimmune diseases and graft-versus-host disease.

10 Claims, 8 Drawing Sheets

(56) References Cited

U.S. PATENT DOCUMENTS

| | | | |
|---|---|---|---|
| 2014/0271820 A1 | 9/2014 | McGhee | |
| 2015/0050329 A1 | 2/2015 | Metselaar | |
| 2015/0174070 A1* | 6/2015 | Cheng | A61K 31/496 424/450 |
| 2015/0265642 A1 | 9/2015 | Sinclair et al. | |
| 2016/0058793 A1* | 3/2016 | Terman | A61K 35/17 424/277.1 |

FOREIGN PATENT DOCUMENTS

| | | |
|---|---|---|
| JP | 2013-529638 | 7/2013 |
| WO | 00/42989 | 7/2000 |
| WO | 2005/046643 | 5/2005 |
| WO | 2005/107712 | 11/2005 |
| WO | 2011/160110 | 12/2011 |
| WO | 2014/159760 | 10/2014 |
| WO | 2015/017807 | 2/2015 |

OTHER PUBLICATIONS

Panwar, P. et al., "Preparation, Characterization, and in Vitro Release Study of Albendazole-Encapsulated Nanosize Liposomes". International Journal of Nanomedicine. 2010. vol. 5; p. 101, introduction; p. 102, first column, fourth paragraph, second column, first paragraph.

Extended European search report issued in EP Application No. 16864923.4, dated May 14, 2019.

Search Report dated Apr. 8, 2019 in Singapore Application No. 11201803915U.

Thangasamy, A., et al., "Recepteur d'Origine Nantais Tyrosine Kinase Is a Direct Target of Hypoxia-inducible Factor-1a-mediated Invasion of Breast Carcinoma Cells", (J. Biol chem., 2009, vol. 284 No. 21, p. 14001-14010.

* cited by examiner

ECHINOMYCIN FORMULATION, METHOD OF MAKING AND METHOD OF USE THEREOF

This application is a National Stage Entry of PCT/US2016/061157, filed Nov. 9, 2016 and claims priority to U.S. Provisional Patent Application No. 62/253,257, filed Nov. 10, 2015. The entirety of all of the aforementioned applications is incorporated herein by reference.

FIELD

This application relates generally to compositions and methods for preparing and delivering liposomal echinomycin formulations for the treatment of proliferative disorders, autoimmune diseases and alloimmune responses.

BACKGROUND

Hypoxia-inducible factors (HIF) are transcriptional factors and mediate the cellular response to hypoxia. HIFs are known to be upregulated in many cancers, autoimmune diseases and alloimmune responses. In particular, HIFs are involved in tumor metabolism, angiogenesis, and metastasis (Semenza, G. L. et al., Nature Rev. Cancer. 2003; 3(10): 721-32).

Echinomycin (NSC526417) is a member of the quinoxaline family originally isolated from *Streptomyces echinatus* in 1957. Echinomycin is a small-molecule that inhibits the DNA-binding activity of HIF1α. Echinomycin has been shown to exhibit antitumor activity against B16 melanoma and P388 leukemia implanted murine tumors and against growth of human tumor cells in vitro and in vivo. Moreover, echinomycin was shown to efficiently eradicate mouse acute lymphoblastic leukemia and human acute myeloid leukemia in xenogeneic models by preferentially eliminating leukemia stem cells (Wang et al., Cell Stem Cell. 2011; 8(4):399-411).

Echinomycin was brought into clinical trials by the National Cancer Institute. However, echinomycin as employed in these studies did not demonstrate significant antitumor activity in previously treated patients. Multiple phase I (7-11) and phase II (12-19) trials for solid tumors have been conducted over the years. However, because the drug was not consistently effective for patients with solid tumors that are refractory to all existing therapies, clinical development of echinomycin was halted. Since the studies were carried out long before it was known that echinomycin is a HIF inhibitor (Kong D. et al., Cancer Res. 2005; 65(19):9047-55), the efficacy studies were not designed to evaluate possible benefit of the suppression of HIF. Although echinomycin was used in several phase II trials with a dose of 1200 μg/m$^2$ in humans, no pharmacokinetics (PK) data emerged since no method was available from 1985-95 to measure the drug concentration. However, new methods have emerged recently, revealing that echinomycin has a short half-life in vivo, thereby limiting its clinical use.

Echinomycin is highly insoluble in water, which complicates the means to which the drug can be formulated into a suitable dosage form. When dissolved in water, echinomycin quickly precipitates out of solution and thus any formulation which relies on mixture of the free drug with an aqueous solvent cannot produce significant bioavailability in the recipient therein. Furthermore, the available solvents with which echinomycin can be dissolved in, such as DMSO, are clinically unacceptable because of the harsh nature of these solvents on the patient. Clinical trials for echinomycin also revealed significant reported side effects, such as severe nausea and vomiting, further limiting its clinical utility.

In view of the above-described limitations, there is a need for new and effective echinomycin formulations, which are non-toxic and efficacious against proliferative disorders, autoimmune diseases, graft-versus-host disease or any other diseases in need of HIF-1 suppression.

SUMMARY

One aspect of the present application relates to a liposomal drug formulation for treating a disease in a patient characterized by overexpression of HIF-1α and/or HIF-2α. The liposomal drug formulation contains a plurality of liposomes in a pharmaceutically acceptable carrier. The liposomes encapsulate echinomycin and are made from a PEGylated phospholipid, a neutral phosphoglyceride, and a sterol.

In one embodiment, the PEGylated phospholipid is a distearoylphosphatidylethanolamine-polyethylene glycol (DSPE-PEG), dimyristoyl phosphatidylethanolamine-polyethylene glycol (DMPE-PEG), dipalmitoylglycerosuccinate polyethylene glycol (DPGS-PEG), cholesteryl-polyethylene glycol, or a ceramide-based PEGylated lipid.

In another embodiment, the neutral phosphoglyceride is selected from the group consisting of phosphatidylcholine, phosphatidylserine, phosphatidylethanolamine, phosphatidylglycerol and phosphatidylinositol.

In another embodiment, the molar ratio of the PEGylated phospholipid to total lipids in the formulation is from 3 to 6%; the molar ratio of the neutral phosphoglyceride to total lipids in the formulation is between 45 to 60% %; and the molar ratio of the sterol to total lipids in the formulation is between 30 to 50% %.

In one embodiment, the PEGylated phospholipid is distearoylphosphatidylethanolamine-polyethylene glycol (DSPE-PEG), the neutral phosphoglyceride is phosphatidylcholine, and the sterol is cholesterol.

In a particular embodiment, the liposomes comprise 5.3% DSPE-PEG-2000, 56.3% hydrogenated soybean phosphatidylcholine (HSPC) and 38.4% cholesterol.

In certain embodiments, the mass ratio of echinomycin to total lipids is between 2 to 10%. In a particular embodiment, the mass ratio of echinomycin to total lipids is 5%.

In some embodiments, at least 90% of the liposomes in the formulation have a diameter between 80 to 120 nm.

In some embodiments, the average polydispersity index of the liposomes is <0.1 and the liposomes and are sufficiently stable to achieve a shelf-life of at least 12 months at 4° C.

In other embodiments, the liposomes are formulated as a lyophilized powder.

In another aspect, a method for treating a disease in a patient characterized by overexpression of HIF-1α and/or HIF-2a with a PEGylated liposomal formulation according to the present application includes administering the PEGylated formulation to a patient in need thereof, wherein the liposomal formulation comprises echinomycin in an amount sufficient to treat the disease.

In one embodiment, the disease is a proliferative disorder. In a particular embodiment, the proliferative disease is leukemia. In another embodiment, the proliferative disorder is breast cancer.

In another embodiment, the disease is an autoimmune disease.

In another embodiment, the disease is graft-versus-host disease.

In a further aspect, a method for making a PEGylated liposomal formulation according to the present application includes forming a mixture comprising echinomycin and the lipid components, including the PEGylated phospholipid, the neutral phospholipid and the sterol in a polar solvent; drying the mixture so as to remove the polar solvent, thereby forming a dried lipid film; solubilizing the dried lipid film in a buffer to form a lipid suspension; extruding the lipid suspension through a polycarbonate filter to achieve a desired size range of liposomes; and sterilizing the liposomes by filtration.

DETAILED DESCRIPTION

Figure 1:
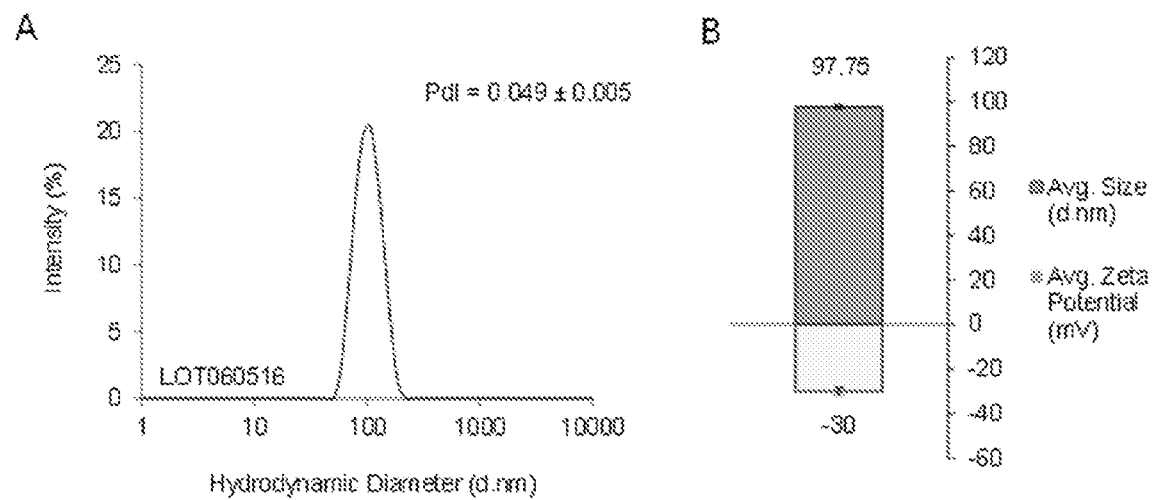
FIG. 1. Physical characteristics of liposomal echinomycin. (A) Size distribution for a typical preparation measured by dynamic light scattering (DLS) on Malvern Zetasizer software. (B) Summary of average size and zeta potential of liposomal echinomycin. Data is summary of 6 independent preparations +/−s.d. Measurements were performed using Malvern Zetasizer software FIG. 2. In vitro release of echinomycin from liposomal echinomycin. (Panel A) Drug release curve of liposomal echinomycin dialyzed against ddH$_2$O at 21° C. Data points represent averages +/−s.d. of triplicate measurements by HPLC. (Panel B) Representative HPLC chromatograms indicating echinomycin peaks at corresponding time-points plotted in (Panel A).

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

As used herein, the term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm or tumor, which is an abnormal growth of tissue. "Cancer" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancer of the brain, bladder, breast, cervix, colon, head and neck, kidney, lung, non-small cell lung, mesothelioma, ovary, prostate, stomach and uterus, leukemia, and medulloblastoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

As used herein, the term "autoimmune disease" refers to a condition in which the immune system of an individual (e.g., activated T cells) attacks the individual's own tissues and cells. The term "alloimmune response" refers to a condition in which the immune system of an individual attack implanted tissue or cells (as in a graft or transplant).

Exemplary autoimmune diseases for treatment with the methods of the instant disclosure include arthritis, alopecia greata, ankylosing spondylitis, autoimmune hemolytic anemia, autoimmune hepatitis, Behcet's disease, Crohn's disease, dermatomyositis, diabetes (Type I), glomerulonephritis, Grave's disease, Guillain-Barre syndrome, inflammatory bowel disorder (IBD), lupus nephritis, multiple sclerosis, myasthenia gravis, myocarditis, pemphigus/pemphigoid, pernicious anemia, polyarteritis nodosa, polymyositis, primary biliary cirrhosis, psoriasis, rheumatoid arthritis, rheumatic fever, sarcoidosis, scleroderma, Sjogren's syndrome, systemic lupus erythematosus (SLE), thyroiditis (such as Hashimoto's thyroiditis and Ord's thyroiditis), ulcerative colitis, uveitis, vitiligo, and Wegener's granulomatosis. Exemplary alloimmune responses for treatment with the methods of the instant disclosure include graft-versus-host disease (GVHD) and transplant rejection.

As used herein, "treatment" means any amelioration of the proliferative disorder, autoimmune disease or alloimmune response.

The terms "treat" and "treatment" refer to the amelioration of one or more symptoms associated with a cell proliferative disorder, autoimmune disease or alloimmune response; prevention or delay of the onset of one or more symptoms of a cell proliferative disorder, autoimmune disease or alloimmune response; and/or lessening of the severity or frequency of one or more symptoms of cell proliferative disorder, autoimmune disease or alloimmune response.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same disease or disorder as the individual being treated, who is about the same age as the individual being treated (to ensure that the stages of the disease in the treated individual and the control individual(s) are comparable). The individual (also referred to as "patient" or "subject") being treated may be a mammalian subject, preferably a human subject, such as a fetus, infant, child, adolescent, or adult human.

Microemulsion Echinomycin Drug Delivery Systems

The present application provides a microemulsion echinomycin drug delivery system for the treatment of proliferative disorders, autoimmune diseases, and alloimmune responses in which HIF-1α or HIF-2α is elevated. An emulsion is a mixture of two or more liquids that are normally immiscible (unmixable or unblendable). The microemulsion echinomycin drug delivery system may comprise liposomes, micelles or a mixture of liposomes and micelles. A liposome is a spherical vesicle with an aqueous solution core surrounded by a hydrophobic membrane, in the form of a lipid bilayer. Liposomes are most often composed of phospholipids, especially phosphatidylcholine, but may also include other lipids, so long as they are compatible with lipid bilayer structure. A typical micelle is a spherical vesicle formed by a single layer of amphiphilic molecules with the hydrophilic "head" regions of the amphiphilic molecules in contact with surrounding solvent, sequestering the hydrophobic single-tail regions in the center of the micelle.

The present application provides liposomal compositions encapsulating echinomycin or an echinomycin analogue, and methods of using such compositions for the treatment of proliferative disorders, autoimmune diseases, and alloimmune responses in which HIF-1α or HIF-2α is elevated. The echinomycin or echinomycin analogue formulations are preferably administered to a patient using a microemulsion drug-delivery system. Unless otherwise noted, the phrase "echinomycin formulation" should be interpreted to include microemulsion formulations containing echinomycin or an echinomycin analogue.

In preferred embodiments, the microemulsion drug-delivery system used is a liposomal drug delivery system. In other embodiments, the microemulsion drug-delivery system used are composed of microparticles (or microspheres), nanoparticles (or nanospheres), nanocapsules, block copolymer micelles, or other polymeric drug delivery systems. In further embodiments, the drug delivery system used is a polymer-based, non-microemulsion drug delivery system such as hydrogels, films or other types of polymeric drug delivery system. In yet further embodiments, the echinomycin or echinomycin analogues are parenterally administered in a lipid-based solvent.

The methods of the present invention are useful for the treatment of proliferative disorders, autoimmune diseases and alloimmune responses in all mammalian subjects, particularly human patients. As used herein, a "patient" is a human patient.

Echinomycin (NSC526417) is a member of the quinoxaline family originally isolated from *Streptomyces echinatus*. Echinomycin is a small-molecule that inhibits the DNA-binding activity of HIF-1α. Echinomycin is soluble in ethanol, alkalis, ketones, acetic acid and chloroform. It is insoluble in water. Echinomycin is therefore lipophilic, and generally readily associates with lipids, e.g., many of those used in the microemulsion drug-delivery systems of the present invention. In certain embodiments, echinomycin can also be formulated as a metal chelate.

Echinomycin analogues include compounds which due to their structural and functional similarity to echinomycin, exhibit effects on reduction of HIF-1α or HIF-2α activity, similar to that of echinomycin. Exemplary echinomycin analogues include YK2000 and YK2005 (Kim, J. B. et al., Int. J. Antimicrob. Agents, 2004 December; 24(6):613-615); Quinomycin G (Zhen X. et al., Mar. Drugs, 2015 Nov. 18; 13(11):6947-61); 2QN (Bailly, C. et al., Anticancer Drug. Des., 1999 June; 14(3):291-303); and quinazomycin (Khan, A. W. et al., Indian J. Biochem., 1969 December; 6(4):220-1).

Microemulsion drug delivery vehicles, including liposomes, can be used to deliver echinomycin or echinomycin analogues in cells or in patients with proliferative disorders or autoimmune diseases, or in patients exhibiting alloimmune responses in e.g., GVHD. Echinomycin or echinomycin analogues can be encapsulated (or incorporated) in any suitable microemulsion drug delivery vehicle that is capable of delivering the drug to target cells in vitro or in vivo.

As used herein, a microemulsion drug delivery vehicle is one that comprises particles that are capable of being suspended in a pharmaceutically acceptable liquid medium wherein the size range of the particles ranges from several nanometers to several micrometers in diameter. The microemulsion drug delivery systems contemplated by in the present application include those that substantially retain their microemulsion nature when administered in vivo. Microemulsion drug delivery systems include, but are not limited to, lipid-based and polymer-based particles. Examples of microemulsion drug delivery systems include liposomes, nanoparticles, (or nanospheres), nanocapsules, microparticles (or microspheres), and block copolymer micelles.

Liposomes bear many resemblances to cellular membranes and are contemplated for use in connection with the present invention as carriers for echinomycin and echinomycin analogues. They are widely suitable as both water- and lipid-soluble substances can be encapsulated, i.e., in the aqueous spaces and within the bilayer itself, respectively. The liposomal formulation of the liposome can be modified by those of skill in the art to maximize the solubility of echinomycin or any of its analogues based on their hydrophobicity.

Liposomes suitable for delivery of echinomycin or echinomycin analogues include those composed primarily of vesicle-forming lipids. Appropriate vesicle-forming lipids for use in the present invention include those lipids which can form spontaneously into bilayer vesicles in water, as exemplified by the phospholipids.

Selection of the appropriate lipids for liposomes is governed by the factors of: (1) liposome stability, (2) phase transition temperature, (3) charge, (4) non-toxicity to mammalian systems, (5) encapsulation efficiency, (6) lipid mixture characteristics. It is expected that one of skill in the art who has the benefit of this disclosure could formulate liposomes according to the present invention which would optimize these factors. The vesicle-forming lipids of this type are preferably ones having two hydrocarbon chains, typically acyl chains, and a head group, either polar or nonpolar. The hydrocarbon chains may be saturated or have varying degrees of unsaturation. There are a variety of synthetic vesicle-forming lipids and naturally-occurring vesicle-forming lipids, including phospholipids, phosphoglycerides, glycolipids, such as the cerebrosides and gangliosides, sphingolipids, ether lipids, sterols, and caged phospholipids.

The liposome includes a liposomal shell composed of one or more concentric lipid monolayers or lipid bilayers. Thus, the lipid shell can be formed from a single lipid bilayer (i.e., the shell may be unilamellar) or several concentric lipid bilayers (i.e., the shell may be multilamellar). The lipids can be synthetic, semi-synthetic or naturally-occurring lipids, including phospholipids, tocopherols, steroids, fatty acids, glycoproteins such as albumin, anionic lipids and cationic lipids. The lipids may have an anionic, cationic or zwitterionic hydrophilic head group, and may be anionic, cationic lipids or neutral at physiologic pH.

Liposomal formulations may include a mixture of lipids. The mixture may comprise (a) a mixture of neutral and/or zwitterionic lipids; (b) a mixture of anionic lipids; (c) a mixture of cationic lipids; (d) a mixture of anionic lipids and cationic lipids; (e) a mixture of neutral or zwitterionic lipids and at least one anionic lipid; (f) a mixture of neutral or zwitterionic lipids and at least one cationic lipid; or (g) a mixture of neutral or zwitterionic lipids, anionic lipids, and cationic lipids. Further, the mixture may comprise saturated lipids, unsaturated lipids or a combination thereof. If an unsaturated lipid has two tails, both tails can be unsaturated, or it can have one saturated tail and one unsaturated tail. In some embodiments, the mixture of lipids does not contain any unsaturated lipids.

In one embodiment, the lipid formulation is substantially free of anionic lipids, substantially free of cationic lipids, or both. In another embodiment, the lipid formulation is free of anionic lipids or cationic lipids or both. In one embodiment, the lipid formulation comprises only neutral lipids. Typically, a neutral lipid component is a lipid having two acyl groups (i.e., diacylphosphatidylcholine and diacylphosphatidylethanolamine). Lipids having a variety of acyl chain groups of varying chain length and degree of saturation are commercially available or may be isolated or synthesized by well-known techniques.

Exemplary neutral or zwitterionic phospholipids include, but are not limited to egg phosphatidylcholine (EPC), egg phosphatidylglycerol (EPG), egg phosphatidylinositol (EPI), egg phosphatidylserine (EPS), phosphatidylethanolamine (EPE), egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidyl choline (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), 1-palmitoyl-2-myristoyl phosphatidylcholine (PMPC), 1-myristoyl-2-palmitoyl phosphatidylcholine (MPPC), dioleoylphosphatidylcholine (DOPC), dimyristoylphosphatidylcholine (DMPC), distearoylphosphatidylcholine (DSPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), dilauryloylphosphatidylcholine (DLPC), palmitoylstearoylphosphatidylcholine (PSPC), lysophosphatidylcholine (LPC), dilinoleoylphosphatidylcholine (DLPC), distearoylphophatidylethanolamine (DSPE), dimyristoylphosphatidylethanolamine (DMPE), dipalmitoyl phosphatidylethanolamine (DPPE), dioleylphosphatidylethanolamine (DOPE), dioleoyl phosphatidylethanolamine (DOPE), palmitoyloleoyl phosphatidylethanolamine (POPE), and palmitoylstearoylphosphatidylglycerol (PSPG), sterols, such as cholesterol and ergosterol; cholesterol esters, ceramides, cerebrosides, diacylglycerol, sphingosine, sphingomyelins, such as brain sphingomyelin, egg sphingomyelin, dipalmitoyl sphingomyelin, and distearoyl sphingomyelin dihydrosphingomyelin; and single acylated phospholipids, such as like mono-oleoyl-phosphatidylethanol amine (MOPE).

Zwitterionic lipids include, but are not limited to, acyl zwitterionic lipids and ether zwitterionic lipids. Examples of useful zwitterionic lipids are 1,2-dipalmitoyl-sn-glycero-3-phosphocholine (DPPC), 1,2-distearoyl-sn-glycero-3-phosphocholine (DSPC), 1,2-distearoyl-sn-glycero-3-phosphoethanolamine (DSPE), 1,2-dioleoyl-sn-glycero-3-phosphocholine (DOPC), 1,2-dioleoyl-sn-glycero-3-phosphatidylethanolamine (DOPE), 1,2-diphytanoyl-sn-glycero-3-phosphoethanolamine (DPyPE) and dodecylphosphocholine.

Exemplary anionic lipids include dihexadecylphosphate (DhP), phosphatidylinositols, phosphatidylserines, including diacylphosphatidylserines, such as dimyristoylphosphatidylserine, dipalmitoylphosphatidylserine; phosphatidylglycerols, such as dimyristoyl phosphatidylglycerol (DMPG), dipalmitoylphosphatidylglycerol (DPPG), distearoyl phosphatidylglycerol (DSPG), dioleoylphosphatidyl glycerol (DOPG), dilauryloylphosphatidyl glycerol (DLPG), distearyloylphosphatidyl glycerol (DSPG), and lysylphosphatidylglycerol (LPG); phosphatidylethanolamines, such as N-dodecanoyl phosphatidyl ethanoloamine, N-succinyl phosphatidylethanolamine, N-glutaryl phosphatidylethanolamine; phosphatidic acids, including diphosphatidyl glycerol and diacylphosphatidic acids, such as dimyristoyl phosphatic acid and dipalmitoyl phosphatic acid; cardiolipin, and cholesterol hemisuccinate (CHEMS).

Cationic lipids typically have a lipophilic moiety, such as a sterol, an acyl or diacyl chain, and where the lipid has an overall net positive charge. Preferably, the head group of the lipid carries the positive charge. Exemplary cationic lipids include N-[1-(2,3-dioleoyloxy)propyl]-N,N,N-trimethyl ammonium salts, also referred to as TAP lipids, for example as a methylsulfate salt. Suitable TAP lipids include, but are not limited to, DOTAP (dioleoyl-), DMTAP (dimyristoyl-), DPTAP (dipalmitoyl-), and DSTAP (distearoyl-). Other suitable cationic lipids include dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl] cholesterol (DC-Chol); 2,3-dioleoyloxy-N-(2-(sperminecarboxamido)-ethyl)-N,N-dimethyl-1-propanaminium trifluoro-acetate (DOSPA), .β-alanyl cholesterol, cetyltrimethylammonium bromide (CTAB), diC$_{14}$-amidine, N-tert-butyl-N'-tetradecyl-3-tetradecylaminopropionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl (alkenyl)-3-(2-hydroxyethyl)-imidazolinium chloride derivatives, such as 1-[2-(9(Z)-octadecenoyloxy)ethyl]-2-(8 (Z)-heptadecenyl-3-(2-hydroxyethyl)-imidazolinium chloride (DOTIM) and 1-[2-(hexadecanoyloxy)ethyl]-2-pentadecyl-3-(2-hydroxyethyl)imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIC-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), 1,2-disteryloxypropyl-3-dimethyl-hydroxyethyl ammonium bromide (DMRIE), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA).

Typically, a liposomal formulation according to the present application includes at least one lipid within the liposome that is PEGylated, i.e., the lipid includes a polyethylene glycol moiety. Liposomes including PEGylated lipids will have PEG oriented so that it is present on at least the exterior of the liposome (but some PEG may also be exposed to the liposome's interior i.e. to the aqueous core). This orientation can be achieved by attaching the PEG to an appropriate part of the lipid. For example, in an amphiphilic lipid the PEG would be attached to the hydrophilic head, as it is this head which orients itself to the lipid bilayer's aqueous-facing exterior. PEGylation in this way can be achieved by covalent attachment of a PEG to a lipid using techniques known in the art.

Exemplary PEGylated lipids include, but are not limited to distearoylphosphatidylethanolamine-polyethylene glycol (DSPE-PEG), including DSPE PEG(1000 MW), DSPE PEG (2000 MW) and DSPE PEG (5000 MW); dimyristoyl phosphatidylethanolamine-polyethylene glycol (DMPE-PEG), including DMPE PEG(1000 MW), DMPE PEG(2000 MW) and DMPE PEG (5000 MW); dipalmitoylglycerosuccinate polyethylene glycol (DPGS-PEG), including DPGS-PEG (1000 MW), DPGS (2000 MW) and DPGS (5000 MW); stearyl-polyethylene glycol, cholesteryl-polyethylene glycol, and ceramide-based PEGylated lipids such as, N-octanoyl-sphingosine-1-{succinyl[methoxy(polyethylene glycol) MW]}, designated C8 PEG (MW) ceramide, where MW is 750, 2000, or 5000, or N-palmitoyl-sphingosine-1-{succinyl[methoxy(polyethylene glycol) MW]} or designated C16 PEG (MW) ceramide, where MW is 750, 2000, or 5000. Additional PEGylated lipids can be obtained from Avanti Polar Lipids, Inc. (Alabaster, Ala.).

A liposome of the invention will typically include a large number of PEG moieties, which may be the same or different. The average molecular mass of the PEG in a liposome of the invention is above 350 Da but less than 5 kDa e.g., between 0.35-5 kDa, between 1-3 kDa, between 1-2-6 kDa, between 2-3 kDa, or 4-5 kDa, or preferably 2 kDa (PEG2000). The PEG will usually comprise linear polymer chains but, in some embodiments, the PEG may comprise branched polymer chains.

In some embodiments the PEG may be a substituted PEG e.g., in which one or more carbon atoms in the polymer is substituted by one or more alkyl, alkoxy, acyl or aryl groups.

In other embodiments the PEG may include copolymer groups e.g., one or more propylene monomers, to form a PEG polypropylene polymer.

In certain embodiments, the liposome is formed from a mixture of one or more PEGylated phospholipids and one or more additional neutral lipids. The molar percentage of the PEGylated lipids may be between 0.1-20%. In some embodiments, the molar percentage of the PEGylated lipids is between 1-9%, between 2-8%, and preferably between 5-6% of the total lipids in the composition.

As used herein, the "molar percentage" of lipid A in a mixture containing lipids A, B and C is defined as:

$$\frac{\text{molar amount of } A}{\text{molar amount of } A + \text{molar amount of } B + \text{molar amount of } C} \times 100\%$$

In another embodiment, the liposome is formed from a lipid mixture comprising a PEGylated phospholipid, a neutral phosphoglyceride, such as a phosphatidylcholine, phosphatidylserine, phosphatidylethanolamine, phosphatidylglycerol, or phosphatidylinositol; and a neutral sterol, such as cholesterol or ergosterol. In this embodiment, the molar percentage of the PEGylated phospholipid may range from 1 to 10% or 3 to 6% of the total lipids; the amount of the neutral phosphoglyceride (to total lipids) may range from 20-60% or 30-50% or 33-43%; and the molar ratio of the neutral sterol may range from 35-75% or 45-65% or 50-60%.

In a particular embodiment, the liposome is formed from a mixture of DSPE-PEG(2000), HSPC, and cholesterol. In this embodiment, the molar percentage of DSPE-PEG(2000) is about 5.3%, the molar percentage of HSPC is about 56.3%, and the molar percentage of cholesterol is about 38.4%.

As an alternative to PEGylation, a lipid may be modified by covalent attachment of a moiety different from PEG. For example, in some embodiments a lipid may include a polyphosphazene. In some embodiments a lipid may include a poly(vinyl pyrrolidone). In some embodiments a lipid may include a poly(acryl amide). In some embodiments a lipid may include a poly(2-methyl-2-oxazoline). In some embodiments a lipid may include a poly(2-ethyl-2-oxazoline). In some embodiments a lipid may include a phosphatidyl polyglycerol. In some embodiments a lipid may include a poly[N-(2-hydroxypropyl)methacrylamide]. In some embodiments a lipid may include a polyalkylene ether polymer, other than PEG.

The fate and disposition of intravenously injected liposomes depend on their physical properties, such as size, fluidity and surface charge. They may persist in tissues for hours or days, depending on their composition, and half lives in the blood range from minutes to several hours. Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core. MLVs typically have diameters of from 0.5 to 4 µm. Sonication of MLVs results in the formation of large unilamellar vesicles (LUVs) with diameters in the range of 50-500 nm or small unilamellar vesicles (SUVs) with diameters less than 50 nm, typically in the range of 200 to 500 Å, containing an aqueous solution in the core.

Larger liposomes, such as MLVs and LUVs, can be taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Liposomes of the present application are preferably SUVs with a diameter in the range of 60-180 nm, 80-160 nm, or 90-120 nm. A liposome of the present application can be part of a liposomal formulation comprising a plurality of liposomes in which liposomes within the plurality can have a range of diameters. In some embodiments, a liposomal formulation comprises at least 80%, at least 90%, or at least 95% of the liposomes have an average diameter in the range of 60-180 nm, 80-160 nm, 90-120 nm. Also, the diameters within the plurality may have a polydispersity index <0.2, <0.1 or <0.05. In some embodiments, the average diameter of the liposomes are determined using the Malvern Zetasizer method.

One way of increasing the circulation time of liposomes is by using liposomes derivatized with a hydrophilic polymer chain or polyalkylether, such as polyethyleneglycol (PEG)(See e.g., U.S. Pat. Nos. 5,013,556, 5,213,804, 5,225, 212 and 5,395,619). The polymer coating reduces the rate of uptake of liposomes by macrophages and thereby prolongs the presence of the liposomes in the blood stream. This can also be used as a mechanism of prolonged release for the drugs carried by the liposomes. Accordingly, liposomal echinomycin formulations according to the present application preferably include one or more PEGylated lipids.

One of skill in the art can select vesicle-forming lipid(s) that achieve a specified degree of fluidity or rigidity. The fluidity or rigidity of the liposome can be used to control factors such as the stability of the liposome in serum or the rate of release of the entrapped agent in the liposome. Liposomes having a more rigid lipid bilayer, or a liquid crystalline bilayer, are achieved by incorporation of a relatively rigid lipid. The rigidity of the lipid bilayer correlates with the phase transition temperature of the lipids present in the bilayer. Phase transition temperature is the temperature at which the lipid changes physical state and shifts from an ordered gel phase to a disordered liquid crystalline phase. Several factors affect the phase transition temperature of a lipid including hydrocarbon chain length and degree of unsaturation, charge and headgroup species of the lipid. A lipid having a relatively high phase transition temperature will produce a more rigid bilayer. Other lipid components, such as cholesterol, are also known to contribute to membrane rigidity in lipid bilayer structures. Cholesterol may be used to manipulate the fluidity, elasticity and permeability of the lipid bilayer. It is thought to function by filling in gaps in the lipid bilayer. In contrast, lipid fluidity is achieved by incorporation of a relatively fluid lipid, typically one having a lower phase transition temperature. Phase transition temperatures of many lipids are tabulated in a variety of sources, such as Avanti Polar Lipids catalogue and Lipidat by Martin Caffrey, CRC Press.

Phospholipids can form a variety of structures other than liposomes when dispersed in water, depending on the molar ratio of lipid to water. At low ratios the liposome is the preferred structure. The physical characteristics of liposomes depend on the pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes of the present application may be prepared to have substantially homogeneous sizes in a selected size range. One effective sizing method for REVs and MLVs involves extruding an aqueous suspension of the liposomes through a series of polycarbonate membranes having a selected uniform pore size in the range of 0.03 to 0.2 microns, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in Specialized Drug Delivery Systems-Manufacturing and Production Technology, (P. Tyle, Ed.) Marcel Dekker, New York, pp. 267-316 (1990)). Homogenization relies on shearing energy to fragment large liposomes into smaller ones. Other appropriate methods of down-sizing liposomes include reducing liposome size by vigorous agitation of the liposomes in the presence of an appropriate solubilizing detergent, such as deoxycholate.

Liposomes that have been sized to a range of about 0.2-0.4 microns may be sterilized by filtering the liposomes through a conventional sterilization filter, which is typically a 0.22 micron filter, on a high throughput basis. Other appropriate methods of sterilization will be apparent to those of skill in the art.

Non-toxicity of the lipids is also a significant consideration in the present application. Lipids approved for use in clinical applications are well-known to those of skill in the art. In certain embodiments, synthetic lipids, for example, may be preferred over lipids derived from biological sources due to a decreased risk of viral or protein contamination from the source organism.

The original method of forming liposomes involved first suspending phospholipids in an organic solvent and then evaporating to dryness until a dry lipid cake or film is formed. An appropriate amount of aqueous medium is added and the lipids spontaneously form multilamellar concentric bilayer vesicles (also termed multilamellar vesicles (MLVs). These MLVs can then be dispersed and reduced in size by mechanical means.

In spite of the water-insoluble nature of echinomycin, the inventors of the present application have found that stable liposomes can be formed by combining echinomycin and lipids in a polar solvent, such as ethanol, drying these components to form a film and then dispersing the liposomes in an aqueous medium. Thus, in one embodiment, after echinomycin and the lipids are thoroughly mixed in the organic solvent, the solvent is removed using e.g., a rotary evaporator, thereby resulting in a dried lipid film. The dried lipid film is hydrated and solubilized in a suitable buffer (e.g., PBS, pH 7.4), thereby resulting in a lipid suspension. The lipid suspension is then repetitively extruded through polycarbonate filters using an Avanti Mini-Extruder to achieve a desired size range of liposomes. The liposomes are then sterilized by filtration (0.45- or 0.2-μm sterile filters). Water-soluble echinomycin analogues can be passively entrapped by hydrating a lipid film with an aqueous solution containing the water-soluble echinomycin analogue.

Echinomycin may be localized within the lipid bilayer, between the two leaflets of the lipid bilayer, within the internal core space, upon either face of the bilayer, within or upon the PEG moiety of the liposome, or a combination thereof. An alternate method for creating large unilamellar vesicles (LUVs) is the reverse-phase evaporation process, described, for example, in U.S. Pat. No. 4,235,871. This process generates reverse-phase evaporation vesicles (REVs), which are mostly unilamellar but also typically contain some oligolamellar vesicles. In this procedure a mixture of polar lipid in an organic solvent is mixed with a suitable aqueous medium. A homogeneous water-in-oil type of emulsion is formed and the organic solvent is evaporated until a gel is formed. The gel is then converted to a suspension by dispersing the gel-like mixture in an aqueous media.

In alternate embodiment, echinomycin or echinomycin analogues may be conjugated to the surface of the liposomal bilayer. In one embodiment, echinomycin is covalently attached to a liposome by amide conjugation. For example, phospholipids with hydroxyl functional groups can be conjugated to one of the amine groups present in echinomycin or one of its analogues.

Liposomal formulation according to the present invention will have sufficient long-term stability to achieve a shelf-life of at least 3 months, at least 6 months, at least 12 months, at least 24 months or at least 48 months at room temperature or refrigeration temperature (e.g., 4° C.).

In some alternative embodiments, the echinomycin or echinomycin analogue may be encapsulated in a protective wall material that is polymeric in nature rather than lipid-based. The polymer used to encapsulate the bioactive agent is typically a single copolymer or homopolymer. The polymeric drug delivery system may be microemulsion or non-microemulsion in nature.

Microemulsion polymeric encapsulation structures include microparticles, microcapsules, microspheres, nanoparticles, nanocapsules, nanospheres, block copolymer micelles, and the like. Both synthetic polymers, which are made by man, and biopolymers, including proteins and polysaccharides, can be used in the present invention. The polymeric drug delivery system may be composed of biodegradable or non-biodegradable polymeric materials, or any combination thereof.

As used herein, a "microemulsion" refers to an emulsion comprising microspheres that are of regular or semi-regular shape with a diameter of from about 10 nm to 500 μm. In some embodiments, the microemulsion of the present application contains liposomes with diameters in the range of 20-400 nm, 30-300 nm, 50-200 nm, 60-150 nm or 80-120 nm.

In some embodiments, the microemulsion of the present application comprises micelles having a shell composed of a single layer of amphiphilic molecules. The inner core of the micelle creates a hydrophobic microenvironment for non-polar drugs, while the hydrophilic shell provides a stabilizing interface between the micelle core and the aqueous medium. The properties of the hydrophilic shell can be adjusted to both maximize biocompatibility and avoid reticuloendothelial system uptake and renal filtration. The size of the micelles is usually between 10 nm and 100 nm.

Non-microemulsion polymeric drug-delivery systems including films, hydrogels and "depot" type drug delivery systems are also contemplated by the present invention. Such non-microemulsion polymeric systems can also be used in the present invention in conjunction with parenteral injection, particularly where the non-microemulsion drug delivery system is placed in proximity to the targeted cancerous tissue. As used herein, a "hydrogel" means a solution of polymers, sometimes referred to as a sol, converted into gel state by small ions or polymers of the opposite charge or by chemical crosslinking. A "polymeric film" refers to a polymer-based film generally from about 0.5 to 5 mm in thickness which is sometimes used as a coating.

In certain embodiments the liposomes, microparticles, nanoparticles, microcapsules, block copolymer micelles or other polymeric drug delivery vehicles comprising echinomycin or an echinomycin analogue can be coated, conjugated to or modified with a cell-specific targeting ligand. By linking a delivery vehicle to a cell-targeting ligand, delivery of echinomycin can be directed to a target cell population which binds to the cell-targeting ligand or targeting ligand. As used herein, a "targeting ligand" includes any ligand which causes a liposome to associate with the target cell-type to an enhanced degree over non-targeted tissues Targeting ligands, such as antibodies or antibody fragments can be used to bind to the liposome surface and to direct the antibody and its drug contents to specific antigenic receptors located on a particular cell-type surface (See e.g., Mastrobattista et al., 1999). Carbohydrate determinants (glycoprotein, lectin and glycolipid cell-surface components that play a role in cell-cell recognition, interaction and adhesion) can also be used as targeting ligands as they have potential in directing liposomes to particular cell types. Certain proteins can be used as targeting ligands, usually ones that are recognized by self-surface receptors of the targeted tissue. For example, a ligand that binds to a cell-surface receptor that is overexpressed in particular cancer cells might be used to increase uptake of liposomes by the target tissue. Cell surface receptors that are endocytosed will be preferred in certain embodiments. When combined with PEGylated liposomes, the targeting ligand is often attached to the end of the hydrophilic polymer that is exposed to the aqueous medium. Alternately, liposomes can incorporate fusogenic proteins, e.g., fusogenic proteins derived from viruses, which induce fusion of the liposome with the cellular membrane.

In certain embodiments, the targeting ligand is a cell surface receptor that is endocytosed by the target cell. Appropriate targeting ligands for use in the present application include any ligand that causes increased binding or association of liposomes with cell-surface of the target cells over non-target cells. The targeting ligand can be a small molecule, peptide, ligand, antibody fragment, aptamer or synbody. A synbody is a synthetic antibody produced from a library comprised of strings of random peptides screened for binding to target proteins of interest and are described in U.S. 2011/0143953. An aptamer is a nucleic acid version of an antibody that comprises a class of oligonucleotides that can form specific three dimensional structures exhibiting high affinity binding to a wide variety of cell surface molecules, proteins, and/or macromolecular structures. Exemplary cell targeting ligands include, but are not limited to, small molecules (e.g., folate, adenosine, purine) and large molecules (e.g., peptide or antibody) that bind to (and target) e.g., epidermal dendritic cells as further described below.

Exemplary antibody or antibody derived fragments may include any member of the group consisting of: IgG, antibody variable region; isolated CDR region; single chain Fv molecule (scFv) comprising a VH and VL domain linked by a peptide linker allowing for association between the two domains to form an antigen binding site; bispecific scFv dimer; minibody comprising a scFv joined to a CH3 domain; diabody (dAb) fragment; single chain dAb fragment consisting of a VH or a VL domain; Fab fragment consisting of VL, VH, CL and CH1 domains; Fab' fragment, which differs from a Fab fragment by the addition of a few residues at the carboxyl terminus of the heavy chain CH1 domain, including one or more cysteines from the antibody hinge region; Fab'-SH fragment, a Fab' fragment in which the cysteine residue(s) of the constant domains bear a free thiol group; F(ab')$_2$, bivalent fragment comprising two linked Fab fragments; Fd fragment consisting of VH and CH1 domains; derivatives thereof; and any other antibody fragment(s) retaining antigen-binding function. Fv, scFv, or diabody molecules may be stabilized by the incorporation of disulphide bridges linking the VH and VL domains. When using antibody-derived fragments, any or all of the targeting domains therein and/or Fc regions may be "humanized" using methodologies well known to those of skill in the art. In some embodiments, the antibody may be modified to remove the Fc region.

Antibody-Echinomycin Drug Conjugates

In another aspect, echinomycin or one of its analogues may be conjugated to a cell binding agent or antibody, such as an anti-cancer antibody described above. As used herein, the phrase "antibody conjugate" or "antibody drug conjugate (ADC)" refers to an antibody conjugated to echinomycin or an analogue thereof via a linker or bi-functional cross-linking agent. Use of an echinomycin/echinomycin analogue-antibody conjugate combines the high specificity of a monoclonal antibody for a tumor-associated antigen with the pharmacological potency of echinomycin or analogue therefrom. Examples of ADCs include gemtuzumab ozogamicin (Mylotarg; anti-CD33 mAb conjugated to calicheamycin, Pfizer/Wyeth); brentuximab vedotin (SGN-35, Adcetris, a CD30-targeting ADC consisting of brentuximab, covalently linked to MMAE (monomethylauristatin), Seattle Genetics); and trastuzumab-DM1 conjugate (T-DM1).

A wide array of linker technologies have been employed for the preparation of antibody-drug conjugates as described in U.S. Pat. No. 9,090,629. Any one of the methods and reagents described therein can be employed in the preparation of the antibody-echinomycin conjugates of the present application. As used herein, a "bifunctional crosslinking reagent" refers to a reagent that possesses two reactive groups; one of which is capable of reacting with a cell-binding agent or antibody, and another which is capable of reacting with echinomycin so as to link the cell-binding agent or antibody with echinomycin, thereby forming a conjugate.

Any suitable bifunctional crosslinking reagent can be used in connection with the present application, so long as the linker reagent provides for retention of the therapeutic activity, e.g., HIF-1α inhibition, and targeting characteristics of the antibody, respectively, without undue toxicity. Preferably, the linker molecule joins echinomycin and/or an echinomycin analogue to the cell-binding agent or antibody through chemical bonds (as described above), such that echinomycin and the cell-binding agent are chemically coupled (e.g., covalently bonded) to each other. The bifunctional crosslinking reagents that can be used for making the drug-linker compounds of the present invention include those described in Thermo Scientific Pierce Crosslinking Technical Handbook.

A linker may be a "cleavable" linker or a "non-cleavable" linker. Cleavable linkers are designed to release the drug when subjected to certain environment factors, e.g., when internalized into the target cell. Cleavable linkers include acid labile linkers, protease sensitive linkers, photolabile linkers, dimethyl linker or disulfide-containing linkers. Non-cleavable linkers tend to remain covalently associated with at least one amino acid of the antibody and the drug upon internalization by and degradation within the target cell.

In one embodiment, the bifunctional crosslinking reagent includes a non-cleavable linker. A non-cleavable linker is any chemical moiety that is capable of linking echinomycin to a cell-binding agent or antibody in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the cytotoxic agent or the cell-binding agent remains active.

Suitable crosslinking reagents that form non-cleavable linkers between echinomycin and the cell-binding agent or antibody are well known in the art. In one embodiment, echinomycin and/or an echinomycin analogue is linked to the cell-binding agent or antibody through a thioether bond. Examples of non-cleavable linkers include linkers having a maleimido- or haloacetyl-based moiety for reaction with the cytotoxic agent. Such bifunctional crosslinking reagents are well known in the art (see e.g., US Patent Application Publication Nos. 2010/0129314), and those available from Pierce Biotechnology Inc. (Rockland, Ill.), including include, but not limited to, N-succinimidyl 4-(maleimidomethyl)cyclohexanecarboxylate (SMCC), N-succinimidyl-4-(N-maleimidomethyl)-cyclohexane-1-carboxy-(6-amido-caproa-te), which is a "long chain" analog of SMCC (LC-SMCC), κ-maleimidoundecanoic acid N-succinimidyl ester (KMUA), γ-maleimidobutyric acid N-succinimidyl ester (GMBS), 6-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)2, BM(PEO) 3, N-(β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodoacetyl)aminobenzoate (sulfo-SIAB), m-maleimidobenzoyl-N-hydroxysulfosuccinimide ester (sulfo-MBS), N-(δ-maleimidobutryloxy)sulfosuccinimde ester (sulfo-GMBS), N-(δ-maleimidocaproyloxy)sulfosuccimido ester (sulfo-EMCS), N-(κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEGn-Mal. Preferably, the bifunctional crosslinking reagent is SMCC.

A solution of an antibody in aqueous buffer may be incubated with a molar excess of an antibody-modifying agent such as N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. The modified antibody is then reacted with a thiol-containing echinomycin derivative to produce a thioether-linked antibody-echinomycin conjugate. The antibody-cytotoxic conjugate is then purified by gel-filtration or other methods mentioned above or by methods known to one of skill in the art. Other cross-linkers that introduce maleimido groups or haloacetyl groups on to a cell binding agent are well known in the art, and include the linkers described above.

Antibody conjugates may include an average of about 1, about 2, about 3, about 4, about 5, about 6, about 7, about 8, about 9, about 10, about 11, about 12, about 13, about 14, about 15, about 16, about 17, about 18, about 19, or about 20 echinomycin molecules (and/or analogues) per antibody.

Combination Therapies.

In certain embodiments, HIF-1α inhibition with the echinomycin formulations of the present application may be combined with standard cancer treatments (e.g., surgery, radiation, and chemotherapy). Such an approach is predicated on the fact that HIFs are known to mediate resistance to radiation therapy and chemotherapy (Semenza, Trends Pharmacol Sci. 2012 April; 33(4): 207-214). For example, evidence indicates that HIF-1 activity may contribute to the development of resistance to novel targeted therapies, such as imatinib treatment of chronic myeloid leukemia. Specifically, HIF-1 appears to mediate resistance to imatinib through metabolic reprogramming, by activating expression of transketolase and thereby increasing glucose flux through the non-oxidative arm of the pentose phosphate pathway. The switch from oxidative to reductive metabolism that is mediated by HIF-1 has the effect of reducing cellular ROS levels, which may increase resistance to cytotoxic chemotherapy (Semenza, 2012).

In certain embodiments, echinomycin or its analogues may be administered in synergistic combinations with one or more other chemotherapeutic or anti-cancer agents. In these instances, it may be possible to reduce the dose of the chemotherapeutic or anti-cancer agents administered. An example of such a combination is echinomycin in combination with imatinib for the treatment of leukemia or the combination of echinomycin in combination with Herceptin for treating breast cancer. It is believed that the combined use of HIF-1α inhibition and chemotherapy can reverse the negative effects of resistance to radiation therapy, chemotherapy, and/or apoptosis, as well as angiogenesis, stem cell maintenance, metabolic reprogramming, autocrine growth factor signaling, epithelial-mesenchymal transition, invasion, and metastasis.

As used herein, the phrase "anti-cancer agent" refers to a "small molecule drug" or a protein or antibody that can reduce the rate of cancer cell growth or induce or mediate the death (e.g., necrosis or apoptosis) of cancer cells in a subject (e.g., a human). The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

The anti-cancer agent may be an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone or anti-hormonal agent; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue or combination thereof.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) and ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormonal or anti-hormonal agents include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); abiraterone acetate (Zytiga); leuprorelin (Lupron); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3K$\alpha$,$\delta$ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055 (AstraZeneca), OSI-027 (OSI), INK-128, BEZ235, PI-103, Torin1, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzomib (PR-171), YU101, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, RO4987655, RO5068760, AZD6244, GSK1120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brmobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BMW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxel.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); and mimosine (Leucenol).

In some embodiments, echinomycin or an echinomycin analogue is administered in synergistic combinations with one or more SOC MTX/calcineurin inhibitor for the treatment of GVHD.

These additional chemotherapeutic agents may be loaded into liposomes with echinomycin or its analogues, in separate liposomal formulations co-administered with the liposomal formulations of the present application, or by other modes of administration as otherwise employed (e.g., oral administration, i. v. injection etc.).

Pharmaceutical Formulations.

Pharmaceutical compositions of the present invention comprising echinomycin or an echinomycin analogue and a microemulsion drug delivery carrier such as a liposome are prepared according to standard techniques. They can further comprise a pharmaceutically acceptable carrier. As used herein, the term "pharmaceutically acceptable" refers to a molecular entity or composition that does not produce an adverse, allergic or other untoward reaction when administered to an animal or a human, as appropriate. The term "pharmaceutically acceptable carrier", as used herein, includes any and all solvents, dispersion media, coatings, antibacterial and/or antifungal agents, isotonic and absorption delaying agents, buffers, excipients, binders, lubricants, gels, surfactants and the like, that may be used as a media for a pharmaceutically acceptable substance.

Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, isotonic aqueous solutions, phosphate buffered saline, dextrose, 0.3% aqueous glycine, glycerol, ethanol and the like, as well as combinations thereof. In many cases, it will be preferable to include isotonic agents, for example, sugars, polyalcohols such as mannitol, sorbitol, or sodium chloride in the composition, or glycoproteins for enhanced stability, such as albumin, lipoprotein and globulin. Pharmaceutically acceptable carriers may further comprise minor amounts of auxiliary substances such as wetting or emulsifying agents, preservatives or buffers, which enhance the shelf life or effectiveness of the therapeutic agents.

These compositions can be sterilized by conventional sterilization techniques that are well-known to those of skill in the art. Sufficiently small liposomes, for example, can be sterilized using sterile filtration techniques.

Formulation characteristics that can be modified include, for example, the pH and the osmolality. For example, it may be desired to achieve a formulation that has a pH and osmolality similar to that of human blood or tissues to facilitate the formulation's effectiveness when administered parenterally. Alternatively, to promote the effectiveness of the disclosed compositions when administered via other administration routes, alternative characteristics may be modified.

Buffers are useful in the present invention for, among other purposes, manipulation of the total pH of the pharmaceutical formulation (especially desired for parenteral administration). A variety of buffers known in the art can be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in parenterally administered forms of the presently disclosed compositions in the present invention include sodium or potassium buffers, including sodium phosphate, potassium phosphate, sodium succinate and sodium citrate.

Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%).

In one embodiment, sodium phosphate is employed in a concentration approximating 20 mM to achieve a pH of approximately 7.0. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used.

Depending upon the dosage form and intended route of administration it may alternatively be advantageous to use buffers in different concentrations or to use other additives to adjust the pH of the composition to encompass other ranges. Useful pH ranges for compositions of the present invention include a pH of about 2.0 to a pH of about 12.0.

In some embodiments, it will also be advantageous to employ surfactants in the presently disclosed formulations, where those surfactants will not be disruptive of the drug-delivery system used. Surfactants or anti-adsorbants that prove useful include polyoxyethylenesorbitans, polyoxyethylenesorbitan monolaurate, polysorbate-20, such as Tween-20™, polysorbate-80, polysorbate-20, hydroxycellulose, genapol and BRIJ surfactants. By way of example, when any surfactant is employed in the present invention to produce a parenterally administrable composition, it is advantageous to use it in a concentration of about 0.01 to about 0.5 mg/ml.

Additional useful additives are readily determined by those of skill in the art, according to particular needs or intended uses of the compositions and formulator. One such particularly useful additional substance is sodium chloride, which is useful for adjusting the osmolality of the formulations to achieve the desired resulting osmolality. Particularly preferred osmolalities for parenteral administration of the disclosed compositions are in the range of about 270 to about 330 mOsm/kg. The optimal osmolality for parenterally administered compositions, particularly injectables, is approximately 3000 sm/kg and achievable by the use of sodium chloride in concentrations of about 6.5 to about 7.5 mg/ml with a sodium chloride concentration of about 7.0 mg/ml being particularly effective.

Echinomycin-containing liposomes or echinomycin-containing microemulsion drug-delivery vehicles can be stored as a lyophilized powder under aseptic conditions and combined with a sterile aqueous solution prior to administration. The aqueous solution used to resuspend the liposomes can contain pharmaceutically acceptable auxiliary substances as required to approximate physical conditions, such as pH adjusting and buffering agents, tonicity adjusting agents and the like, as discussed above.

In other embodiments the echinomycin-containing liposomes or echinomycin-containing microemulsion drug-delivery vehicle can be stored as a suspension, preferable an aqueous suspension, prior to administration. In certain embodiments, the solution used for storage of liposomes or microemulsion drug carrier suspensions will include lipid-protective agents which protect lipids against free-radical and lipid-peroxidative damage on storage. Suitable protective compounds include free-radical quenchers such as alpha-tocopherol and water-soluble iron-specific chelators, such as ferrioxamine.

Echinomycin/echinomycin analogue dosages can be tested in a suitable animal model as further described below. As a general proposition, a therapeutically effective amount of echinomycin, echinomycin analogue or other anti-cancer agent will be administered in a range from about 10 ng/kg body weight/day to about 100 mg/kg body weight/day whether by one or more administrations. In a particular embodiment, each fusion protein or expression vector is administered in the range of from about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In some embodiments, echinomycin is administered at a body surface area (BSA)-based dose of 10-30,000 µg/m$^2$, 100-30,000 µg/m2, 500-30,000 µg/m$^2$, 1000-30,000 µg/m$^2$, 1500-30,000 µg/m$^2$, 2000-30,000 µg/m$^2$, 2500-30,000 µg/m$^2$, 3000-30,000 µg/m$^2$, 3500-30,000 µg/m$^2$, 4000-30,000 µg/m$^2$, 100-20,000 µg/m$^2$, 500-20,000 µg/m$^2$, 1000-20,000 µg/m$^2$, 1500-20,000 µg/m$^2$, 2000-20,000 µg/m$^2$, 2500-20,000 µg/m$^2$, 3000-20,000 µg/m$^2$, 3500-20,000 µg/m$^2$, 100-10,000 µg/m$^2$, 500-10,000 µg/m$^2$, 1000-10,000 µg/m$^2$, 1500-10,000 µg/m$^2$, 2000-10,000 µg/m$^2$, or 2500-10,000 µg/m$^2$.

In other embodiments, echinomycin is administered in the range of about 10 ng to about 100 ng per individual administration, about 10 ng to about 1 µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The fusion protein or expression vector may be administered daily, every 2, 3, 4, 5, 6 or 7 days, or every 1, 2, 3 or 4 weeks.

In other particular embodiments, the amount of echninomycin may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

Dosages can be tested in several art-accepted animal models suitable for a particular proliferative disorder, autoimmune disease or alloimmune response.

The therapeutic agents in the pharmaceutical compositions may be formulated in a "therapeutically effective amount". A "therapeutically effective amount" refers to an amount effective, at dosages and for periods of time necessary, to achieve the desired therapeutic result. A therapeutically effective amount of the liposomal formulation or other microemulsion drug-delivery vehicle may vary depending on the condition to be treated, the severity and course of the condition, the mode of administration, the bioavailability of the particular agent(s), the ability of the delivery vehicle to elicit a desired response in the individual, previous therapy, the age, weight and sex of the patient, the patient's clinical history and response to the antibody, the type of the fusion protein or expression vector used, discretion of the attending physician, etc. A therapeutically effective amount is also one in which any toxic or detrimental effects of the delivery vehicle is outweighed by the therapeutically beneficial effects.

Methods for Administering Echinomycin or Echinomycin Analogues

In one aspect, the microemulsion drug-delivery system of the present invention is used in a method for treating a mammalian subject with a proliferative disorder, autoimmune disease, or exhibiting an alloimmune response.

In one embodiment, a method of treating and/or reducing the severity of a proliferative disorder in a mammalian subject comprises: administering to the subject a pharmaceutical composition comprising a microemulsion drug delivery vehicle comprising echinomycin or an echinomycin analogue in an amount effective for treating and/or reducing the severity of the proliferative disorder in the subject.

In another embodiment, a method of treating and/or reducing the severity of an autoimmune disease in a mammalian subject comprises: administering to the subject a pharmaceutical composition comprising a microemulsion drug delivery vehicle comprising echinomycin or an echinomycin analogue in an amount effective for treating and/or reducing the severity of the autoimmune disease in the subject.

In a further embodiment, a method of preventing the development of GvHD or reducing the severity of GvHD in a mammalian subject receiving an allogeneic hematopoietic stem cell (HSC) transplant comprises: administering to either the subject, the transplanted HSCs, or both, in combination with a pharmaceutical composition comprising a microemulsion drug delivery vehicle comprising echinomycin in an amount effective for preventing or reducing the severity of GvHD in the subject.

When echinomycin or an echinomycin analog is encapsulated in a liposome or other microemulsion drug-delivery vehicle, any effective amount of the echinomycin or echinomycin may be administered. Preferably, the liposomal formulations or other microemulsion drug-delivery vehicles containing echinomycin or an echinomycin analogue are administered by parenteral injection, including intravenous, intraarterial, intramuscular, subcutaneous, intra-tissue, intranasal, intradermal, instillation, intracerebral, intrarectal, intravaginal, intraperitoneal, intratumoral.

Intravenous administration of liposomal echinomycin has been tolerated by mice at doses of approximately 1 mg/kg of body weight and no $LD_{50}$ value has been reached. In contrast, free echinomycin has an $LD_{50}$ value of 0.629 mg/kg.

Other routes of administration include oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

In certain embodiments, the composition can be formulated as a depot preparation. Such long acting formulations may be administered by implantation at an appropriate site or by parenteral injection, particularly intratumoral injection or injection at a site adjacent to cancerous tissue.

Liposomal preparations or other microemulsion delivery vehicles can be lyophilized and stored as sterile powders, preferably under vacuum, and then reconstituted in bacteriostatic water (containing, for example, benzyl alcohol preservative) or in sterile water prior to injection. Pharmaceutical compositions may be formulated for parenteral administration by injection e.g., by bolus injection or continuous infusion.

The delivery vehicle may be administered to the patient at one time or over a series of treatments and may be administered to the patient at any time from diagnosis onwards. The delivery vehicle may be administered as the sole treatment or in conjunction with other drugs or therapies useful in treating the condition in question.

The present invention is further illustrated by the following examples which should not be construed as limiting. The contents of all references, patents and published patent applications cited throughout this application, as well as the Figures and Tables are incorporated herein by reference. Those of skill in the art should, in light of the present disclosure, appreciate that many changes can be made in the specific embodiments which are disclosed and still obtain a like or similar result without departing from the spirit and scope of the invention.

EXAMPLES

Example 1. Preparation of Liposomal Echinomycin Formulations

Lipid components and echinomycin were weighed out on an analytical balance and dissolved in a suitable solvent, such as chloroform/methanol 2:1 (v/v), at the appropriate ratios in a glass scintillation vial and mixed by vortex. A slow stream of nitrogen gas was used to evaporate the organic solvent and produce a homogeneous lipid film on the walls of the glass vial. To prevent gelation, the drying process was carried out at 65° C. The lipid film was hydrated by adding 10% sucrose (w/v) in double distilled water (ddH$_2$O) pre-heated to 65° C., such that the final concentration of total lipids was 7.1 mg/mL. The hydrated mixture was maintained above 65° C. and mixed vigorously by vortex until all of the film was dissolved. The hydrated solution of large multilamellar vesicles (LMV) was extruded extensively across 200 nm, 100 nm, and 50 nm stacked polycarbonate (PC) filters using an Avanti Mini-Extruder in 1 mL increments until the average size of the liposomes in the pooled post-extrusion mixture was determined by dynamic light scattering (DLS) to be within the range of 94-99 nm, with a polydispersity index (PdI) of less than 0.05. In order to prevent membrane fouling, the extrusion process was carried out at 65° C., and the PC membranes were changed between each 1 mL increment. The minimum number of extrusion passes per 1 mL increment was 21×, but additional passes against a 50 nm PC membrane were employed if the DLS quality criteria measures were not met following analysis of the post-extruded mixture. The resultant suspension of small unilamellar vesicles (SUV) was allowed to stabilize overnight at room temperature (21° C.). The product was then sterile filtered once through a 33 mm diameter 0.22 µm PES membrane (Millipore) to remove unentrapped echinomycin, and the filtrate was sampled for HPLC and DLS analysis and stored in sterile glass vials at 2-8° C. until use.

1.1. Preparation of DSPC-Echinomycin Formulation.

To 1.25 mL 0.2 mg/mL of echinomycin dissolved in chloroform, 1.25 mL 13.75 mg/mL Distearoylphosphatidylcholine (DSPC) in chloroform is added into a round bottom flask. Next, 1.25 mL of 9.8 mg/mL cholesterol dissolved in chloroform is added and mixed gently for 5-10 seconds by hand swirling. Next, the chloroform is evaporated under vacuum in a rotary evaporator for 45 minutes at maximum rotation speed until a lipid film containing echinomycin is formed on the walls of the flask and all solvent has completely evaporated. The film is rehydrated with 5 mL of lipid buffer and vortexed vigorously for 45 minutes to produce a heterogeneous mixture of liposomes. The mixture is then extruded through a 0.2 micron filter, and the resulting mixture is analyzed via HPLC for encapsulation efficiency.

1.2. Preparation of mPEG-DSPE-DOPC-Echinomycin Formulation.

DSPC can be substituted with DOPC to increase encapsulation efficiency, while mPEG-DSPE can be added to reduce clearance by reticuloendothelial system (RES) and increase circulation time in vivo. In one example, 1.25 mL 0.2 mg/mL of echinomycin was dissolved in chloroform, 25 mL, 13.75 mg/mL 1, 2-Dioleoyl-sn-glycero-3-phosphocholine (DOPC) in chloroform is added into a round bottom flask. Next, 1.25 mL of 9.8 mg/mL cholesterol dissolved in chloroform and 1.25 mL 1.25 mg ml, Poly(ethylenglycol)-α-Distearoyl Phosphatidylethanolamine (mPEG-DSPE)-2000 in chloroform are added and mixed gently for 5-10 seconds by hand swirling. Next, the chloroform is evaporated under vacuum in a rotary evaporator for 45 minutes at maximum rotation speed until a lipid film containing echinomycin is formed on the walls of the flask and all solvent has completely evaporated. The film is rehydrated with 5 mL of lipid buffer to and vortexed vigorously for 45 minutes to produce a heterogeneous mixture of liposomes. The mixture is then extruded through a 0.2 micron filter, and the resulting mixture is analyzed via HPLC for encapsulation efficiency.

1.3. Preparation of mPEG-DSPE-EPC-HEPC-Echinomycin Formulation.

0.25 mg echinomycin was dissolved in 1.25 ml of chloroform a round bottom flask and a mixture of 12.2 mg/ml egg phosphatidylcholine (EPC), 2.28 mg/ml hydrogenated egg phosphatidylcholine (HEPC), 2.28 mg/ml cholesterol and 5.4 mg/ml methoxy polyethylene glycol-distearyloyl phosphatidylethanolamine (mPEG-DSPE) in 1.25 ml of chloroform/methanol is added to the echinomycin solution in the round bottom flask. Once the lipids are thoroughly mixed in the solvent, the solvent is evaporated under vacuum to remove the solvent and form a lipid film on the wall of the round-bottom flask. The film is rehydrated with 5 mL of lipid buffer to and vortexed vigorously for 45 minutes to produce a heterogeneous mixture of liposomes. The mixture is then extruded through a 0.2 micron filter, and the resulting mixture is analyzed via HPLC for encapsulation efficiency.

1.4. Preparation of mPEG-DSPE-HSPC-Echinomycin Formulation.

In another example, a 14 mL batch of liposomal echinomycin was produced as follows: 60 mg of HSPC, 20 mg of DSPE-PEG(2000), and 20 mg of ovine wool cholesterol were dissolved in a 5 mL glass scintillation vial with 4 mL of chloroform/methanol 2:1 (v/v). 0.5 mL of echinomycin 10 mg/mL in chloroform/methanol 2:1 (v/v) was added to the mixture and the mixture was mixed for 30 sec by vortex. The mixture was then heated to 65° C. in a water bath and the organic solvent was evaporated using a slow stream of nitrogen gas and swirling the vial by hand until a homogeneous film containing echinomycin and lipid formed on the walls of the vial. During the process of evaporating the organic solvent, it was critical to maintain the mixture at 65° C. to avoid gelation. Alternatively, a round-bottom flask may be used in an automated evaporator system resting in a heated water bath with spinning; however, for the small lab-scale production lot, it was sufficient to swirl the vial by hand to produce an even film layer. In a small oven, a sufficient volume of hydration solution was pre-heated to 65° C. In this example, the hydration solution was 10% sucrose (w/v) in distilled deionized water (sucDDW), but it is noted that other hydration solutions are acceptable, such as regular DDW, 0.9% saline in DDW or 1×PBS. The lipid-echinomycin film was then hydrated in 14 mL of sucDDW at 65° C. with vigorous mixing by vortex until all of the film was completely dissolved (about 1hr) to produce a white suspension of large multilamellar vesicles (LMV). The hydrated solution of large multilamellar vesicles (LMV) was then extruded extensively across 200 nm, 100 nm, and 50 nm stacked polycarbonate (PC) filters using an Avanti Mini-Extruder in 1 mL increments until the average hydrodynamic diameter of the liposomes in the pooled post-extrusion mixture was determined by dynamic light scattering (DLS) to be within the range of 94-99 nm, with a polydispersity index (PdI) of less than 0.05. In order to prevent membrane fouling, the extrusion process was carried out at 65° C., and the PC membranes were changed between each 1 mL increment. The minimum number of extrusion passes per 1 mL increment was 21×, but additional passes against a 50 nm PC membrane were employed if the DLS quality criteria measures were not met following analysis of the post-extruded mixture. The resultant suspension of small uni-lamellar vesicles (SUV) was allowed to stabilize for 12-15 hrs at room temperature (21° C.). The product was then sterile filtered once through a 33 mm 0.22 µm PES membrane (Millipore) to remove unentrapped echinomycin and other possible contaminants. The filtrate was sampled for HPLC and DLS analysis and stored in sterile glass vials at 2-8° C. until use.

Example 2. Size Distribution and Physical Characterization of Liposomal Echinomycin Liposomal echinomycin formulations were characterized using Malvern Zetasizer software to determine average size and zeta potential. The size distribution was consistently found to be within a very narrow range with a polydispersity index of less than 0.1, as shown in the representative dynamic light scattering (DLS) profile in FIG. 1, panel A. Accumulation of liposomes in tumor tissues by enhanced permeability and retention (EPR) and maximal immunoevasive properties of PEGylated stealth liposomes from rapid uptake by the reticuloendothelial system (RES) has been reported for liposomes <100 nm in size. The average hydrodynamic diameter of liposomal echinomycin was found to be about 98 d·nm; this was easily reproduced between batches (FIG. 1, panel B).

Measurement of zeta potential of liposomal formulations can provide reliable method for predicting particle stability and tendency to aggregate. The average zeta potential of liposomal echinomycin was found to be approximately −30 mV, which suggested that the product was stable and unlikely to aggregate (FIG. 1, panel B). A summary of additional physical characteristics of 6 independent liposomal echinomycin preparations, including PdI, averages, and standard deviation, is shown in Table 1. All data was produced using Malvern Zetasizer software.

TABLE 1

| LOT No. | Hydrodynamic Diameter (d · nm) | PdI | Zeta Potential (mV) | Mobility (µmcm/Vs) | Conductivity (mS/cm) |
| --- | --- | --- | --- | --- | --- |
| 42316 | 97.66 | 0.03 | −31.8 | −2.496 | 0.00294 |
| 50416 | 97.54 | 0.063 | −31.3 | −2.45 | 0.01030 |
| 51016 | 98.28 | 0.063 | −29.2 | −2.288 | 0.00295 |
| 51116 | 96.88 | 0.034 | −29.6 | −2.322 | 0.00918 |
| 60516 | 99.11 | 0.049 | −30.8 | −2.414 | 0.00306 |
| 62216 | 97.05 | 0.042 | −27.2 | −2.135 | 0.00789 |
| AVG | 97.75 | 0.047 | −30.0 | −2.351 | 0.00605 |
| STDEV (±) | ±0.83 | ±0.014 | ±1.7 | ±0.131 | ±0.00344 |

Example 3. In Vitro Release of Echinomycin from Liposomal Echinomycin

Figure 2:
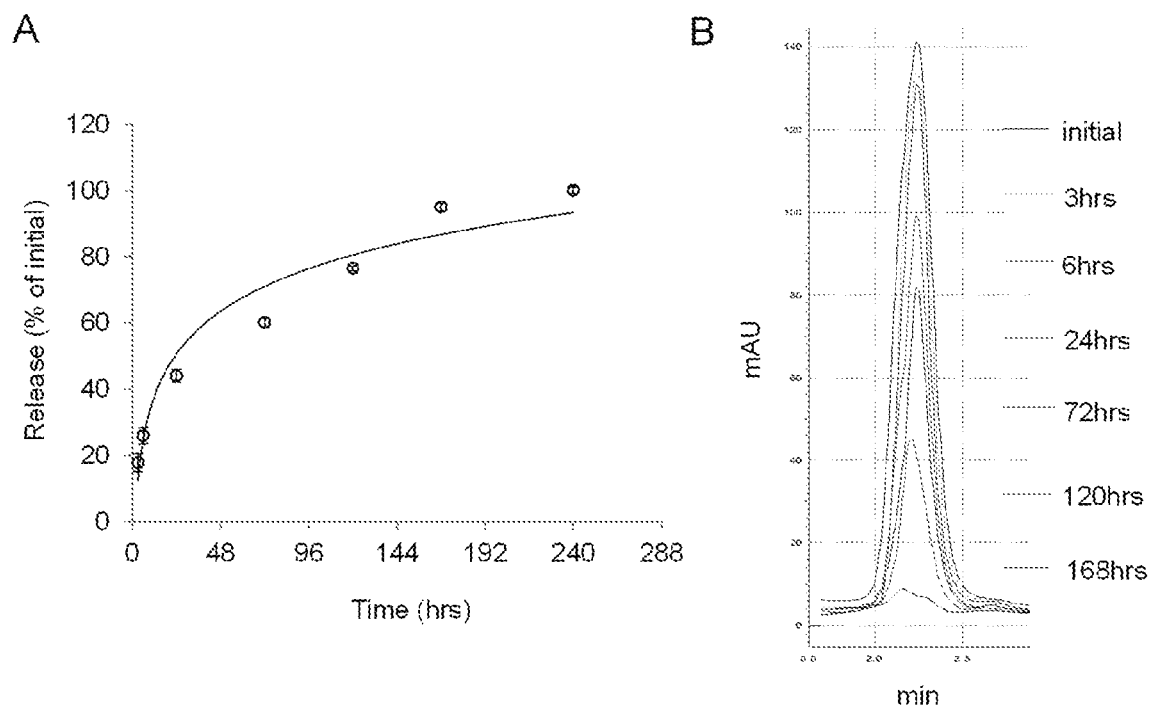

An evaluation of in vitro drug release from liposomal echinomycin was done via dialysis by measuring the release rate of echinomycin over a period of 240 hours by HPLC at each time point at room temperature in water. Echinomycin concentrations were calculated for each time-point according to an echinomycin standard curve. Calculations of percent release were derived as a function of the initial echinomycin concentration detected in the liposomal echinomycin sample before starting dialysis. The in vitro release characteristics of liposomes are summarized in the cumulative percentage release shown in FIG. 2, panel A. Representative HPLC chromatograms showing echinomycin peaks at corresponding time-points are plotted in FIG. 2, panel B.

Example 4. In Vitro Storage and Stability of Liposomal Echinomycin

Figure 3:
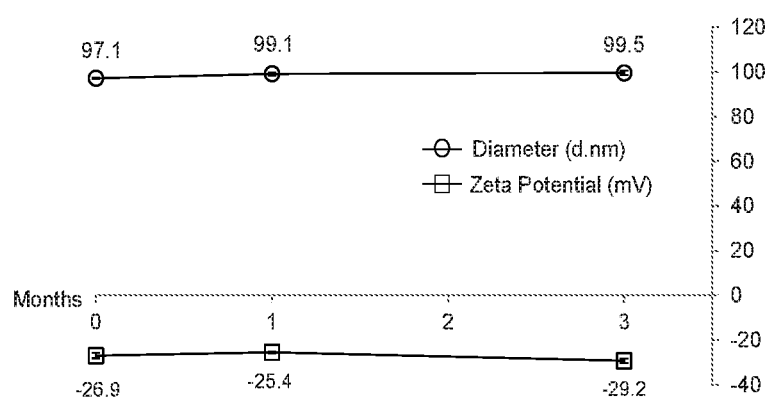
FIG. 3. In vitro liposomal echinomycin storage and stability. (Panel A and Panel B) Liposomal echinomycin was stored at 4° C. and sampled for stability parameters after 1 and 3 months of storage. Zero months indicates measurements taken directly after preparation. Measurements of average size and zeta potential (Panel A) and average polydispersity index (PdI) (Panel B) of liposomal echinomycin during storage at 4° C. Data was generated using Malvern Zetasizer software and error bars represent s.d. of triplicate measurements. (Panel C) HPLC analysis of echinomycin content loss during storage at 4° C. expressed as percent of initial measurement (0 months). Error bars represent s.d. of triplicate measurements.
Figure 3:
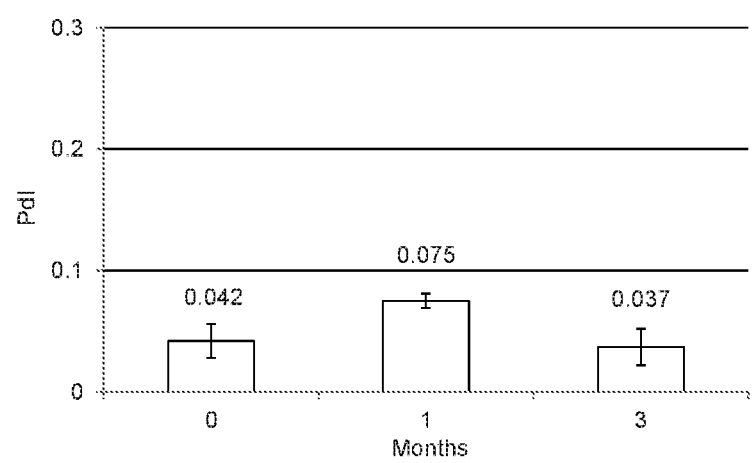
Figure 3:
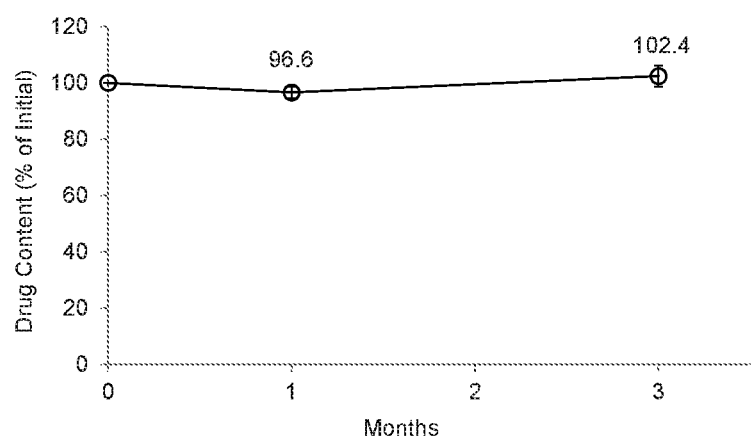

To test the stability of liposomal echinomycin under storage conditions, physical characteristics of liposomal echinomycin was monitored over the course of 3 months at 4° C. Size, PdI, and zeta potential of liposomal echinomycin were evaluated using Malvern Zetasizer software at 1 and 3 months in storage. No considerable change in any of these parameters from the initial measurements were found (FIG. 3, panel A and panel B). Drug content loss of liposomal echinomycin was tested by removal of accumulated drug precipitate by filtration through 0.22 PES membrane at 1 and 3 month time-points. Upon HPLC analysis of the filtrate, no evidence of any drug leakage or precipitation from liposomes under storage conditions was found.

Example 5. Liposomal Echinomycin Toxicity in Mice

Figure 4:
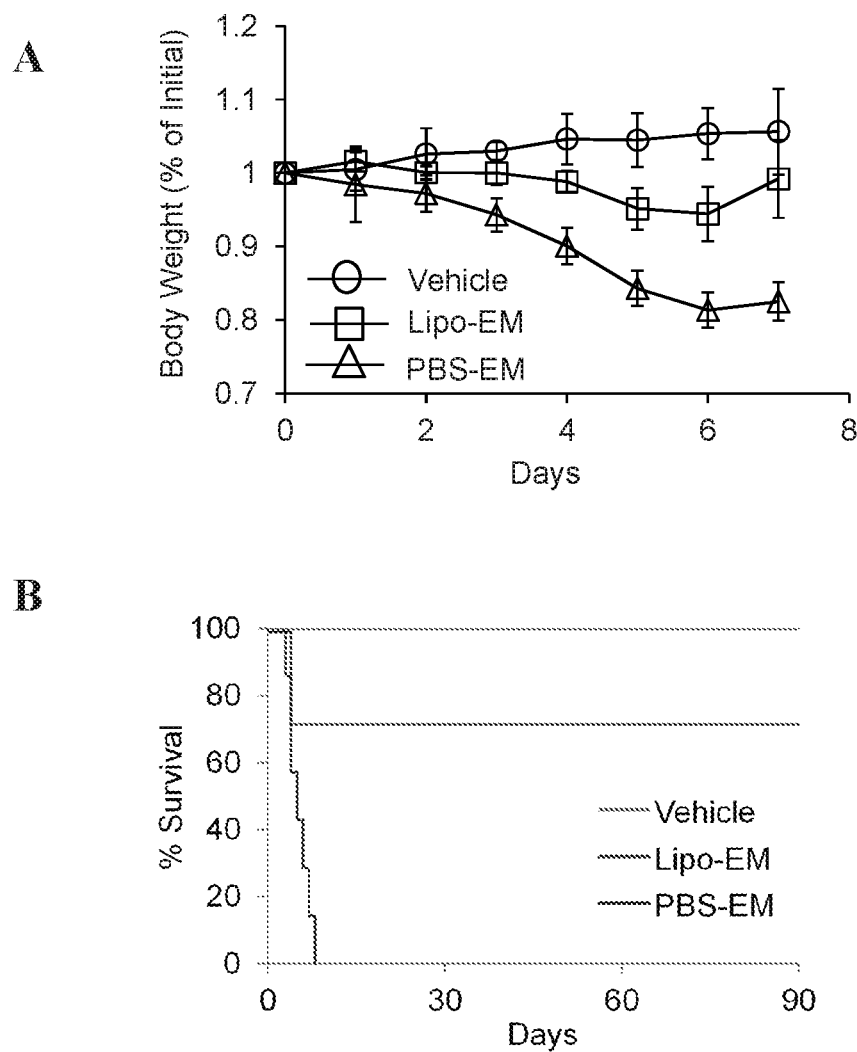
FIG. 4. Comparison of toxicity and efficacy for liposomal vs. free echinomycin. (Panel A) Body weight change in female NSG mice receiving a therapeutic cycle of liposomal echinomycin, PBS echinomycin (20% DMSO in PBS), or equivalent dosage of empty liposomal vehicle. Mice were treated with 250 μg/kg of liposomal (n=7) or free (n=7) echinomycin, or vehicle equivalent (n=4), by i.v. once every other day for a total of 3 doses). (Panel B) Survival of NSG mice administered single i.v. injection of 1 mg/kg liposomal or free echinomycin, or equivalent dosage of empty liposomal vehicle.

To test the toxicity of liposomal echinomycin in mice, a therapeutic cycle of echinomycin was administered at a dose of 250 µg/kg, (liposomal-formulated, non-liposomal-formulated, or equivalent dosage of empty liposomal vehicle) by i.v. injection, every other day for a total of 3 doses. Body weights of the mice were monitored throughout this period. The results of this analysis showed that mice receiving liposomal echinomycin lost less weight and recovered the lost weight faster than mice receiving the equivalent dosage and schedule of free echinomycin (FIG. 4, panel A). At higher drug doses (1 mg/kg), all free echinomycin-treated mice died within a week, while 70% of mice receiving echinomycin-loaded liposome survived over the entire observation period of 3+ months (FIG. 4, panel B).

Figure 5:
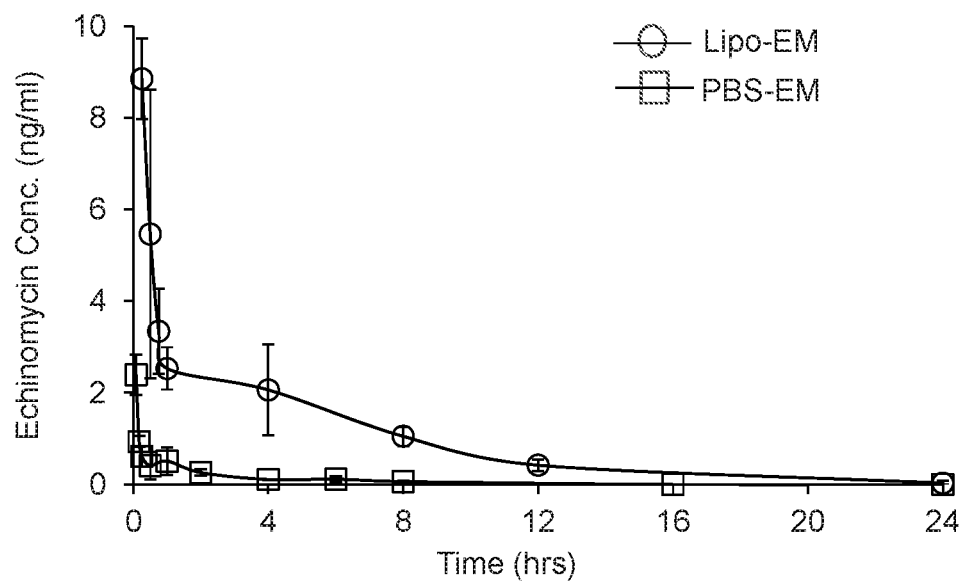
FIG. 5. Comparison of pharmacokinetics for liposomal vs. free echinomycin. Serum plasma levels of echinomycin detected by MS following single dose i.v. administration of 0.1 mg/kg liposomal echinomycin or free echinomycin FIG. 6. Accumulation of Echinomycin in tumor. Concentration of echinomycin in breast tumor SUM 159 following single dose i.v. injection (0.1 mg/kg) of liposomal and conventionally formulated echinomycin. n=3/time-point.

Example 6. Pharmacokinetics of Liposomal Echinomycin Vs. Free Echinomycin in Mice "Stealth" liposomes are known to exhibit prolonged circulation time in the bloodstream compared to their free drug counterparts, owing to the presence of PEG moieties on the liposome surface. PEG shields liposomes from rapid uptake by the RES and provides steric stabilization to the liposome particles. To measure the prolonged circulation of liposomal echinomycin in the bloodstream compared to free echinomycin, the pharmacokinetics of both formulations were evaluated by detecting echinomycin levels in the plasma by mass spectrometry following single i.v. injections of 0.1 mg/kg of liposomal echinomycin or free echinomycin in mice (FIG. 5). The results of this analysis indicated that concentrations and circulation times of echinomycin in the blood were significantly increased in mice receiving liposomal echinomycin compared to equivalent doses of free echinomycin. In particular, the data show that a plasma concentration >1 ng/ml is achieved only at 15 min after administration of 0.1 mg/kg of free echinomycin but the same dose of liposomal echinomycin maintained this concentration for over 8 hrs following administration (FIG. 5).

Figure 6:
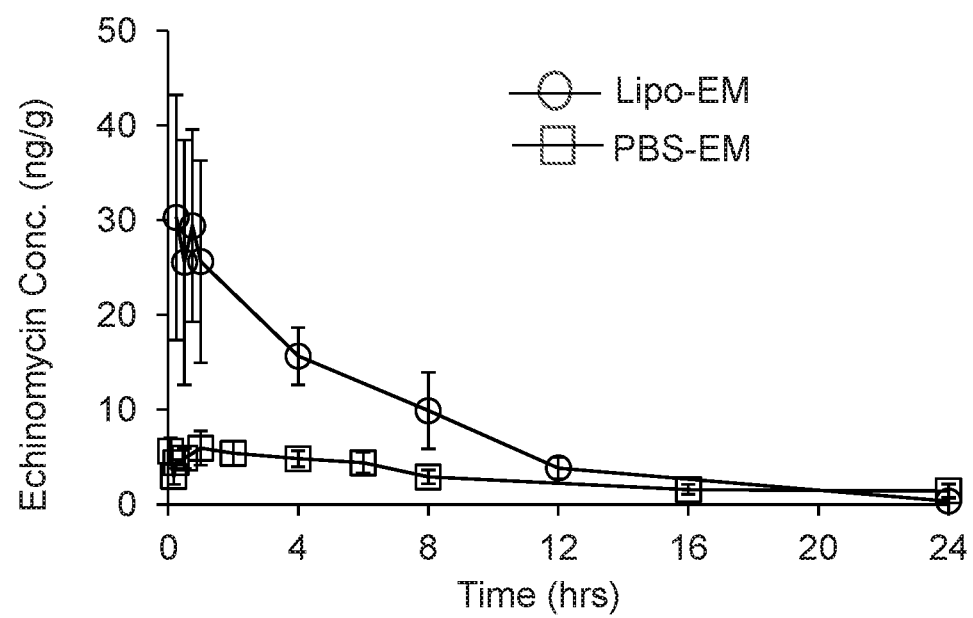

Additionally, the pharmacokinetics of conventional and liposomal formulated echinomycin in breast cancer tissues of NSG mice were evaluated and found to be significantly increased. As shown in FIG. 6, a tumor concentration >5 ng/g can be achieved only at 2 hrs post-dosing of conventional echinomycin. In contrast, administration of liposomal echinomycin (Lipo-EM) at the same dose of 0.1 mg/kg achieved a tissue concentration >5 ng/g, which was prolonged for more than 10 hrs following administration (FIG. 6). More importantly, peak drug levels in the liposomal echinomycin-treated group were approximately 6-fold higher than those treated with free echinomycin.

Example 7. Basis for Treating ALL with Echinomycin

Early T-cell precursor acute lymphoblastic leukemia (ETP ALL) has been recently recognized as a form of T-cell ALL (T-ALL) with poor prognosis (Coustan-Smith et al., Lancet Oncol., 2009 February; 10(2):147-156). ETP ALL is characterized with a very early differentiation arrest and unique genetic and transcriptional features that are most related to hematopoietic stem cells and myeloid progenitors. Although the immunophenotype, gene expression profile, and gene mutational spectrum for ETP ALL has been characterized, the molecular mechanism for ETP ALL pathobiology is poorly understood and effective therapeutic targets remain to be identified.

Previously, a spontaneous mouse model of T-ALL used to identify leukemia stem cells revealed that, even under normoxia, HIF1α signaling was selectively activated in the stem cells of mouse T-ALL and human AML (Wang Y. et al., Cell Stem Cell. 2011; 8(4):399-411). Recent studies have confirmed that the pathway is also critical for the maintenance of chronic myeloid leukemia stem cells. Importantly, the HIF1α inhibitor echinomycin efficiently eradicated mouse leukemia and was highly effective and selective in eliminating AML stem cells both in vitro and in vivo (Wang et al. 2011). These studies indicated that HIF1α activated a subset of cells present in ETP ALL cells under normoxia, and that echinomycin treatment significantly reduced the ETP ALL cells in xenografted NSG mice (See FIGS. 1, 2 and 3 in Wang et al. 2011). These observations demonstrate that aberrant activation of HIF1α in a normoxic environment represents a unique feature of ETP ALL. To the extent that ETP ALL has transcriptional features that are most related to stem cells and myeloid progenitors and has elevated expression of HIF-1α and its target genes, these features support targeting HIF-1α with liposomal echinomycin for the treatment of ETP ALL.

Figure 7:
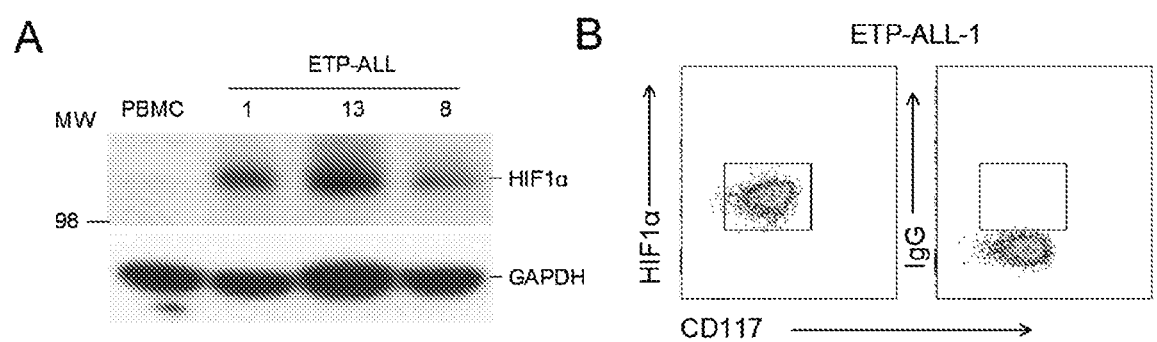
FIG. 7. Accumulation of HIF-1α in ETP-ALL. (Panel A) Levels of HIF-1α protein in the spleens of ETP ALL xenograft models were measured by Western blot. (Panel B) ETP-ALL-1 cells from the spleen of xenograft mice were stained with anti hCD45 and CD117 surface markers and intracellularly stained with APC-conjugated HIF-1α antibody, followed by FACS analysis.

Example 8. Therapeutic Effects of Liposomal Echinomycin Administration in Xenografted ETP-ALL NSG Mice As expected from the results in Example 7, HIF1α proteins were found to be overproduced in ETP ALL cells compared to PBMC control samples from patients with ETP-ALL (FIG. 7, panel A and panel B). High accumulation of HIF-1α was detected in 3 ETP-ALL samples by western blot analysis (FIG. 7, panel A) or by intracellular staining of HIF1α followed by FACS analysis (FIG. 7, panel B). These results confirm that aberrant activation of HIF1α is present in human primary ETP ALL cells under normoxia.

Figure 8:
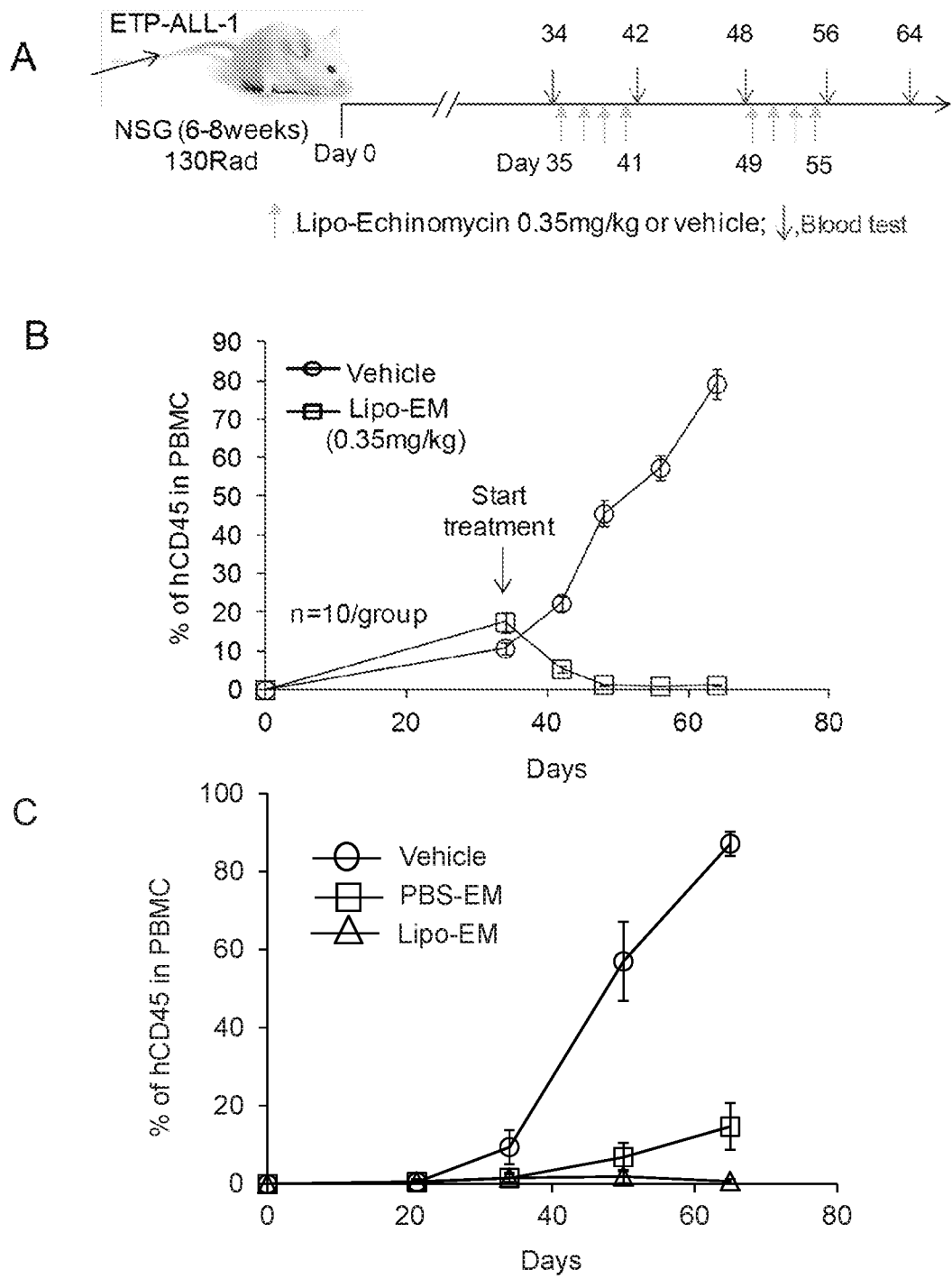
FIG. 8. Liposomal echinomycin eliminates human ETP-ALL cells in a xenograft mouse model. (Panel A) Dosing regimen of liposomal echinomycin treatment for ETP-ALL humanized mice for data in panel B. Day 0 indicates day of transplantation with human ETP-ALL-1 cells. Green arrows represent one individual liposomal echinomycin injection (0.35 mg/kg/injection via i.v.). Red arrows indicate blood tests. (Panel B) NSG mice with 1.3 Gys irradiated were given i.v. injection of 1×10$^6$ human ETP-ALL-1 cells. Human CD45$^+$ cells in PBMC of recipients were detected by FACS analysis at day 34 after transplantation. The percentage of human CD45$^+$ in PBMC of recipient mice before treatment (Day 34) and after treatment (Day 42, 48, 56, and 64) of mice (vehicle and liposomal echinomycin treatment) was analyzed by FACS analysis. Summary of percentage of human CD45$^+$ in PBMC of all recipient mice treated with vehicle or liposomal echinomycin (n=10 for each group). (Panel C) At well-tolerated doses, liposomal echinomycin is more effective than maximally free echinomycin. NSG mice were irradiated 1.3 Gys and given i. v. injection of 1×10$^6$ human ETP-ALL-1 cells. FACS analysis was performed on day 21 before treatment. On day 22, mice received the first dose of treatment. One group of recipient mice (PBS-EM, n=5) received 3 cycles of echinomycin in PBS (15 total doses). In each cycle, mice received echinomycin in PBS, at the dose of 0.1 mg/kg by i.v. injection, once every day for a total of 5 doses, followed by 5 days of rest prior to the start of the next cycle. In another group of recipients (Lipo-EM, n=5), mice received 0.35 mg/kg of liposomal echinomycin by i.v. injection. Liposomal echinomycin was administered once every 4 days for the first 2 doses starting on day 22, followed by 7 days of rest. Then mice received an injection every other day for 4 doses, followed by 7 days of rest, and completed with an injection every other day for 4 more doses (10 doses in total). An additional group of mice received empty liposomal vehicle (n=5) according to the same schedule in which the liposomal echinomycin was administered. The percentage of human CD45$^+$ in PBMC of recipients after echinomycin treatment (Day 34, 50, and 65) of mice was analyzed by FACS analysis.

To test whether administration of liposomal echinomycin (Lipo-EM) could eliminate human ETP-ALL cells in vivo, Lipo-EM was administered to xenografted ETP-ALL NSG mice according to the dosing schedule outlined in FIG. 8, panel A. Briefly, 1×10⁶ ETP ALL-1 cells were transplanted via i.v. injection into 1.3 Gys irradiated NSG mice. Reconstitution of the human ETP-ALL cells was monitored by detection of hCD45 in the peripheral blood of recipient mice. The results of this analysis showed that about 10 to 20% of the human CD45$^+$ cells were detected in the blood of recipient mice at day 34 after transplantation. A 20 day Lipo-EM treatment regimen consisting of two cycles with 4 consecutive treatments of every other day as one cycle, separated by 8 days of rest in between cycles commenced on day 35. The percentage of human ETP ALL-1 cells was monitored after treatment. The results of this analysis showed that Lipo-EM significantly reduced ETP-ALL cells in the blood of the xenografted mice (FIG. 8, panel B). In particular, FACS plots depicting the percentage of human ETP ALL cells before administration and at three time-points after Lipo-EM treatment revealed that the average percentage of human CD45 in vehicle mice was 10.73% at day 34, increasing to 22.35% at day 42, 45.61% at day 48, 57.44% at day 56 and finally reaching 80.18% at day 64 in the blood. However, in the Lipo-EM-treated mice, ETP-ALL-1 cells were almost completely eliminated by this treatment regimen such that the percentage of human CD45 cells decreased from 17.47% before treatment to 1.19% after treatment at day 64 in the blood of recipient mice. These results demonstrate the capacity of liposomal echinomycin to effectively eliminate ETP-ALL cells in xenografted mice.

To compare the efficacy of liposomal echinomycin with free echinomycin in this mouse xenograft model for ETP-ALL, 1×10⁶ ETP ALL-1 cells were transplanted via i.v. injection into 1.3 Gys irradiated NSG mice. Lipo-EM treatment was initiated on day 22, when the % hCD45+ cells in the peripheral blood reached approximately 1% according to FACS analysis on day 21. The mice were split into 3 groups of 5 mice per group. All treatments were performed by i.v. injection. The first group received 15 total doses of echinomycin in PBS divided into 3 identical cycles. In each cycle, mice received 0.1 mg/kg of echinomycin in PBS once every day for a total of 5 doses, followed by 5 days of rest prior to the start of the next cycle. The second group received 10 total doses of Lipo-EM in which the first 2 doses were administered once every 4 days, followed by 7 days of rest, then followed by 4 doses every other day, followed by 7 more days of rest, and then 4 more doses administered once every other day. An additional group of mice received empty liposomal vehicle (n=5) according to the same schedule in which the Lipo-EM was administered. Peripheral blood was examined on days 34, 50, and 65 by FACS analysis to compare the growth of ETP-ALL-1 cells in the recipients over the course of treatment (FIG. 8, panel C). The results of this analysis showed that while treatment with echinomycin in PBS did inhibit the growth rate of ETP-ALL-1 cells, treatment with Lipo-EM provided superior efficacy compared to the former (FIG. 8, panel C).

Example 9. Effects of Echinomycin in Breast Cancer Cells In Vitro

Figure 9:
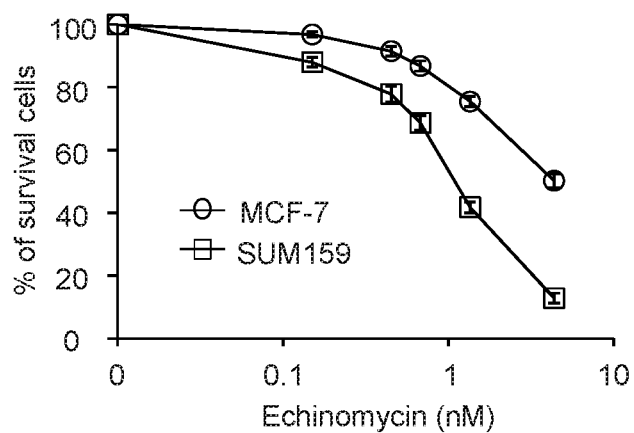
FIG. 9. Echinomycin reduced the number of live breast cancer cells in vitro. Breast cancer cells with high (SUM 159) or low (MCF7) levels of HIF-1α were treated with various concentrations of echinomycin in vitro. The correlation between echinomycin concentration and relative proportions of surviving cells after co-culturing with echinomycin is shown. SUM 159 cells with high HIF-1α are more sensitive to echinomycin than MCF7, which express less HIF-1α.

To better understand the importance of high HIF-1α expression in breast cancer cells, the ability of echinomycin to reduce survival of breast cancer cells was tested in two breast cancer cell lines, MCF7 and SUM 159. More specifically, MCF7 and SUM 159 were treated with different concentrations of echinomycin for 48 hrs, followed by MTT assays to measure cell viability thereafter. The results of this analysis showed that echinomycin reduced the number of live SUM159 cells ($IC_{50}$=1 nM). In contrast, MCF7 cells are less sensitive to echinomycin (FIG. 9). These data suggest that cancer that over-express the HIF protein are more sensitive to Echinomycin.

Figure 10:
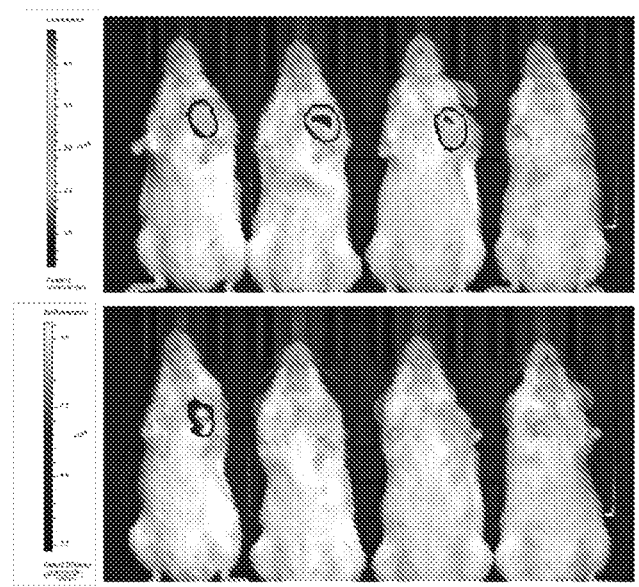
FIG. 10. Accumulation of echinomycin in xenografted breast cancer cells. Human breast cancer cell line SUM-159 was transfected with luciferase and orthotopically xenografted in the mammary fat pads of female NSG mice. DiR-labeled liposomes or free DiR in water was administered to the xenografted mice according to the key at the bottom of the figure. Bioluminescence imaging was used to evaluate luciferase expression in xenografted cells (upper panel) and presence of liposomal echinomycin by bioluminescence imaging (lower panel).

Example 10. Therapeutic Effects of Liposomal Echinomycin in Breast Cancer Cells In Vivo To determine if Lipo-EM allows for efficacious delivery of echinomycin to breast cancer tumor sites, mice bearing luciferase-expressing SUM 159 tumor xenografts were administered D-luciferin to visualize the tumor masses by bioluminescence. In addition, Lipo-EM was labeled with the fluorescent dye, 1,1'-dioctadecyltetramethyl indotricarbocyanine iodide (DiR), enabling the tracking and accumulation of liposomes in vivo. Tumor growth was tracked by endogenously expressed luciferase activity. The results of this analysis show selective accumulation of Lipo-EM in the human breast cancer SUM159 tumors when imaged 24 hrs after administration of the fluorescently labeled liposomal echinomycin. In contrast, administration of an equivalent dose of free DiR dye in water produced no appreciable accumulation or fluorescent signal in the fluorescence channel. Importantly, the mouse without any tumor had no appreciable accumulation of liposome in other organs (FIG. 10). These data demonstrate that Lipo-EM can selectively accumulate in the xenograft tumors of human breast cancer in mice.

Figure 11:
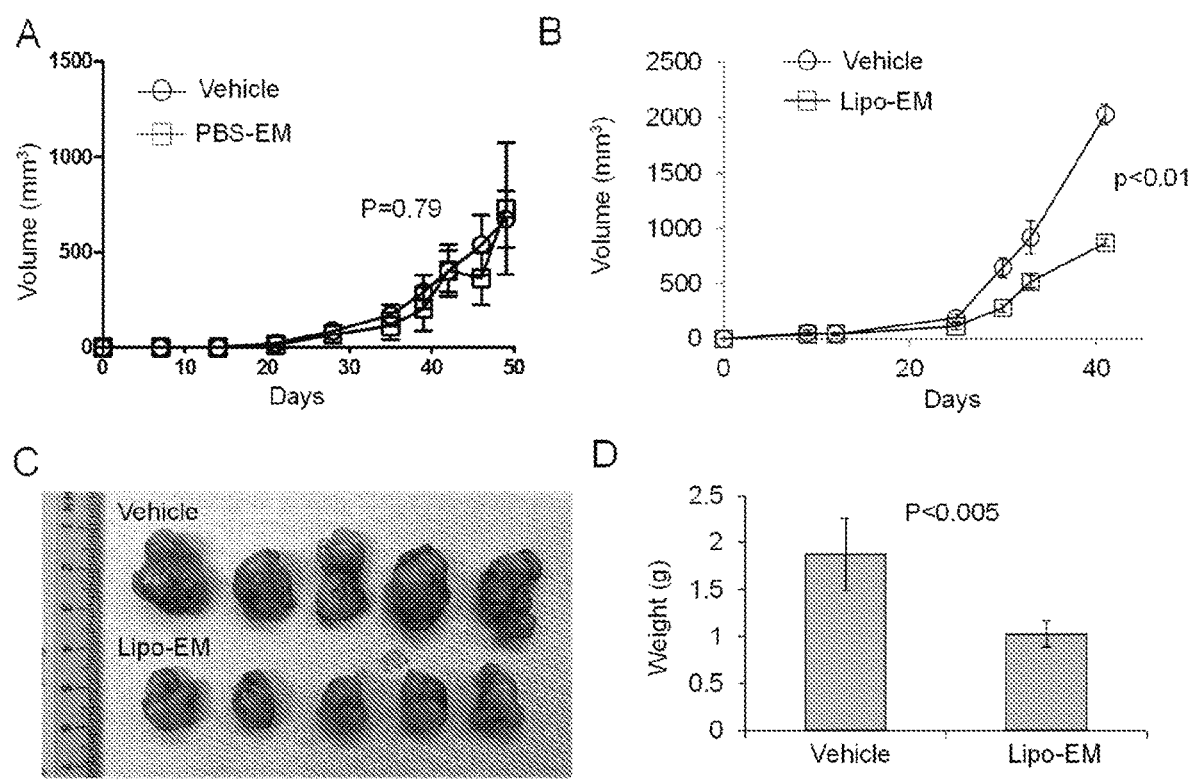
FIG. 11. Therapeutic effect of liposomal echinomycin on breast cancer in vivo. (Panel A) Female NSG mice were xenografted with human SUM159 breast cancer cells and treated with free echinomycin or vehicle (n=10 per group). Mice received 0.1 mg/kg of free echinomycin or vehicle via i.v. injection once every 3 days starting on day 28 for a total of 6 doses. Growth kinetics of SUM159 are shown. (Panel B) Female NSG mice were xenografted with SUM159 breast cancer cells and treated with liposomal echinomycin or vehicle (n=5 per group). The growth kinetics of SUM159 in recipient mice treated with vehicle and liposomal echinomycin are shown. Mice received 0.35 mg/kg of liposomal echinomycin or vehicle by i.v. injection on days 9, 11, 13, 25 and 27. Average tumor volume was recorded throughout the experiment. Error bars represent ±SEM. Individual treatments and dosage are denoted by asterisks. (Panel C) Mice were euthanized, and tumors were dissected and photographed. (Panel D) Summary of tumor weight of breast cancer from vehicle and liposomal echinomycin treated mice. Weight is expressed as average weight ±s.d., P value was calculated by t test.

To test the therapeutic efficacy of free echinomycin (in PBS), Lipo-EM, and vehicle in breast cancer cells in vivo, SUM159 cells were xenografted in the mammary fat pad of NOD-SCID mice. When administered 0.1 mg/kg of free echinomycin, no significant differences in tumor size were observed between the echinomycin treated and vehicle control groups (FIG. 11, panel A). To test the efficacy of Lipo-EM in human breast tumors in vivo, SUM159 breast cancer cells were transplanted into 10 NSG mice in which 5 mice were administered Lipo-EM by i.v. injection at a dose of 0.35 mg/kg on days 9, 11, 13, 25, and 27, and 5 mice were administered a vehicle control (liposome only) at these same time points. In addition, Growth kinetics of the transplanted tumors were measured by volume (FIG. 11, panel B) and by weight (FIG. 11, panel C and panel D). After the tumor size in the vehicle mice reached early removal criteria, the 10 mice were sacrificed, and the tumors were weighed (FIG. 11, panel C and panel D). The results of this analysis show that the growth of tumors in Lipo-EM treated mice receiving only 5 total injections was significantly reduced compared to vehicle-treated mice.

The results of these analyses demonstrate that liposomal echinomycin is a stable formulation that displays reduced toxicity, increased circulation time in the bloodstream, and increased capacity to accumulate in xenografts of human solid tumors in mice, compared to free echinomycin or vehicle controls. Liposomal echinomycin exhibits profound antitumor effects when administered to mice bearing human xenografts of hematopoietic and solid tumor malignancies expressing high levels of HIF-1α.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A PEGylated liposomal drug formulation for treating a disease in a patient, comprising:
   echinomycin;
   a pegylated phospholipid;
   a neutral phosphoglyceride, wherein the neutral phosphoglyceride is hydrogenated soybean phosphatidylcholine (HSPC); and
   a sterol,
   wherein the formulation comprises a plurality of PEGylated liposomes encapsulating the echinomycin,
   wherein the echinomycin is localized within a lipid bilayer of the liposomes,
   wherein the liposomes are suspended in a pharmaceutically acceptable carrier,
   wherein the molar ratio of the PEGylated phospholipid to total lipids in the formulation is between 3% and 6%,
   wherein the molar ratio of the neutral phosphoglyceride to total lipids in the formulation is between 45% and 65%, and
   wherein the molar ratio of the sterol to total lipids in the formulation is between 30% and 50%, and
   wherein the mass ratio of Echinomycin to total lipids is between 2 to 10%
   wherein the formulation does not contain any unsaturated lipids.

2. The formulation of claim 1, wherein the PEGylated phospholipid is a distearoylphosphatidylethanolamine-polyethylene glycol (DSPE-PEG), a dimyristoyl phosphatidylethanolamine-polyethylene glycol (DMPE-PEG), a dipalmitoylglycerosuccinate polyethylene glycol (DPGS-PEG), a cholesteryl-polyethylene glycol, or a ceramide-based pegylated lipid.

3. The formulation of claim 1, wherein the PEGylated phospholipid is a distearoylphosphatidylethanolamine-polyethylene glycol (DSPE-PEG), and the sterol is cholesterol.

4. The formulation of claim 3, comprising DSPE-PEG-2000, and cholesterol.

5. The formulation of claim 4, wherein the molar ratio of DSPE-PEG-2000, HSPC, and cholesterol to total lipids is 5.3%, 56.3%, and 38.4%, respectively.

6. The formulation of claim 1, wherein the mass ratio of echinomycin to total lipids is 5%.

7. The formulation of claim 1, wherein at least 90% of the liposomes in the formulation have a diameter between 80 nm and 120 nm.

8. The formulation of claim 1, wherein the average polydispersity index of the liposomes is <0.1 and the liposomes and are sufficiently stable to achieve a shelf-life of at least 12 months at 4° C.

9. The formulation of claim 1, wherein the liposomes are formulated as a lyophilized powder.

10. A PEGylated liposomal drug formulation, comprising:
    echinomycin;
    a pegylated phospholipid selected from the group consisting of distearoylphosphatidylethanolamine-polyethylene glycol (DSPE-PEG), a dimyristoyl phosphatidylethanolamine-polyethylene glycol (DMPE-PEG), a dipalmitoylglycerosuccinate polyethylene glycol (DPGS-PEG), a cholesteryl-polyethylene glycol, or a ceramide-based pegylated lipid;
    a neutral phosphoglyceride, wherein the neutral phosphoglyceride is hydrogenated soybean phosphatidylcholine (HSPC);

cholesterol, and a pharmaceutically acceptable carrier, wherein the echinomycin, pegylated phospholipid, neutral phosphoglyceride and cholesterol composition form a plurality of PEGylated liposomes suspended in the pharmaceutically acceptable carrier, wherein the echinomycin is localized within a lipid bilayer of the liposomes, wherein the molar ratio of the PEGylated phospholipid to total lipids in the formulation is between 3% and 6%, the molar ratio of the neutral phosphoglyceride to total lipids in the formulation is between 45% and 65%, and the molar ratio of the cholesterol to total lipids in the formulation is between 30% and 50%, and wherein the mass of Echinomycin to total lipids is between 2 to 10% wherein the formulation does not contain unsaturated lipids.

* * * * *